US009464015B2

(12) United States Patent
Dalai et al.

(10) Patent No.: US 9,464,015 B2
(45) Date of Patent: Oct. 11, 2016

(54) PROCESS FOR HYDROGENOLYSIS OF GLYCEROL

(71) Applicant: University of Saskatchewan, Saskatoon (CA)

(72) Inventors: Ajay Kumar Dalai, Saskatoon (CA); Rajesh Vishnudev Sharma, Saskatoon (CA); Pardeep Kumar, Saskatoon (CA)

(73) Assignee: UNIVERSITY OF SASKATCHEWAN, Saskatoon, Saskatchewan (CA)

( * ) Notice: Subject to any disclaimer, the term of this patent is extended or adjusted under 35 U.S.C. 154(b) by 0 days.

(21) Appl. No.: 14/769,112

(22) PCT Filed: Mar. 6, 2014

(86) PCT No.: PCT/CA2014/050183
§ 371 (c)(1),
(2) Date: Aug. 20, 2015

(87) PCT Pub. No.: WO2014/134733
PCT Pub. Date: Sep. 12, 2014

(65) Prior Publication Data
US 2016/0002129 A1   Jan. 7, 2016

Related U.S. Application Data

(60) Provisional application No. 61/774,140, filed on Mar. 7, 2013.

(51) Int. Cl.
| | |
|---|---|
| *C07C 29/60* | (2006.01) |
| *B01J 23/00* | (2006.01) |
| *B01J 23/86* | (2006.01) |
| B01J 37/03 | (2006.01) |
| B01J 37/18 | (2006.01) |
| B01J 38/12 | (2006.01) |
| B01J 23/94 | (2006.01) |
| B01J 35/00 | (2006.01) |
| B01J 35/10 | (2006.01) |

(52) U.S. Cl.
CPC .............. *C07C 29/60* (2013.01); *B01J 23/002* (2013.01); *B01J 23/868* (2013.01); *B01J 23/94* (2013.01); *B01J 35/002* (2013.01); *B01J 35/006* (2013.01); *B01J 35/0066* (2013.01); *B01J 35/1014* (2013.01); *B01J 35/1038* (2013.01); *B01J 35/1061* (2013.01); *B01J 37/03* (2013.01); *B01J 37/18* (2013.01); *B01J 38/12* (2013.01); *B01J 2523/00* (2013.01); *Y02P 20/584* (2015.11)

(58) Field of Classification Search
CPC .................................................... C07C 29/60
USPC ........................................................ 568/861
See application file for complete search history.

(56) References Cited

U.S. PATENT DOCUMENTS

| 5,214,219 A | 5/1993 | Casale et al. |
| 5,276,181 A | 1/1994 | Casale et al. |
| 8,273,924 B2 * | 9/2012 | Henkelmann ........... C07C 29/60 568/861 |
| 2010/0179346 A1 * | 7/2010 | Klein ...................... C07C 29/60 560/129 |

FOREIGN PATENT DOCUMENTS

| CN | 101239315 B | 5/2011 |
| WO | 2011138643 A2 | 5/2012 |

OTHER PUBLICATIONS

International Search Report and Written Opinion of corresponding PCT/CA2014/050183 dated Jul. 8, 2014.
Ma, Zhiqiang, et al., "A non-alkoxide sol-gel route to highly active and selective Cu—Cr catalysts for glycerol conversion", J. Mater. Chem, 2010, 20, 755-760.
Roy, Debdut et al., "Aqueous phase hydrogenolysis of glycerol to 1,2-propanediol without external hydrogen addition", Catal.Today, 2010, 156, 31-37.
Zhenle, Yuan et al., "Biodiesel derived glycerol hydrogenolysis to 1,2-propanediol on Cu/MgO catalysts", Bioresour. Technol., 2010, 101, 7088-7092.
Mane, Rasika, B., et al. "Cu: Al nano catalyst for selective hydrogenolysis of glycerol to 1,2-propanediol", Catal Lett., 2010, 135, 141-147.
Korolev, Yu. A., et al, "Glycerol dehydroxylation in hydrogen on a raney cobalt catalyst", Catalysis in Industry, 2010, vol. 2, No. 3, 287-289.
Chaminand, Julien, et al., "Glycerol hydrogenolysis on heterogenous catalysts", Green. Chem., 2004, 6, 359-361.
Ueda, Naoyuki et al., "Conversion of glycerol to ethylene glycol over Pt modified Ni catalyst", Chem. Lett., 2010, 39, 506-507.
Bolado, Silvia et al, "Glycerol hydrogenolysis to 1,2 propanediol over Ru/C catalyst", Catalysis Comm., 2010, 12, 122-126.
Miyazawa, Tomohisa, et al, "Glycerol hydrogenolysis to 1,2-propanediol catalyzed by a heat-resistant ion-exchange resin combined with Ru/C", Appl. Catal., A., 2007, 329, 30-35.
Gandarias, I., et al., "Hydrogenolysis of glycerol to propanediols over a Pt/ASA catalyst: The role of acid and metal sites on product selectivity and the reaction mechanism", Appl. Catal. B., 2010, 97, 248-256.
Torres, Arely, et al. "Kinetic modeling of aqueous-phase glycerol hydrogenolysis in a batch slurry reactor", Ind. Eng. Chem. Res., 2010, 49, 10826-10835.
Bienholz, A., et al., "Selective hydrogenolysis of glycerol over copper catalysts both in liquid and vapour phase: Correlation between the copper surface area and the catalyst's activity", Appl. Catal. A., 2011, 391, 153-157.
Balaraju, M., et al., "Surface and structural properties of titania-suported Ru catalysts for hydrogenolysis of glycerol", Appl. Catal. A., 2010, 384, 107-114.

* cited by examiner

Primary Examiner — Elvis O Price
(74) Attorney, Agent, or Firm — Bereskin & Parr LLP/S.E.N.C.R.L., s.r.l.; Patricia Folkins

(57) ABSTRACT

A process for the hydrogenolysis of glycerol to produce propylene glycol as the major product comprising contacting the glycerol with hydrogen in the presence of a heterogeneous catalyst under conditions for the formation of propylene glycol is disclosed. In particular, propylene glycol is formed with a selectivity of greater than about 90%.

23 Claims, 23 Drawing Sheets

A B C

PROCESS FOR HYDROGENOLYSIS OF GLYCEROL

CROSS-REFERENCE TO RELATED APPLICATIONS

This application is a National Stage of co-pending International Application No. PCT/CA2014/050183 filed Mar. 6, 2014 which claims the benefit of priority from U.S. provisional application No. 61/774,140 filed on Mar. 7, 2013, the contents of both of which are incorporated herein by reference in their entirety.

FIELD OF THE APPLICATION

The present application is in the field of catalytic hydrogenolysis of glycerol, in particular for the production of propylene glycol.

BACKGROUND OF THE APPLICATION

Industrialization and population growth increases the petroleum demand. The reserved fossil fuel is rapidly diminishing that increases crude oil prices affecting growth of industrialization. This has motivated scientists to look for alternative energy sources which are renewable, economical and environmentally friendly. As an example, there is an increased interest in converting abundantly available biomass to produce valuable chemicals and fuels.[1]

Biodiesel is one of the potential environmentally friendly substitutes for petroleum based diesel fuel. The transesterification of vegetable oil is an example of a process to produce biodiesel which has already been commercialized.[1,2] The global market for biodiesel is estimated to reach 180 million tons by 2016 and to grow at the rate of 42% per year.[3,4] In the biodiesel production process, glycerol is produced in the amount of 10% of the products of the process.[5] Glycerol has been considered as one of the top 12 building block chemicals by the U.S. Department of Energy and can replace some of the chemicals derived from fossil fuel.[4,5,6,7] The large amount of glycerol produced by the biodiesel industry is currently not completely utilized by chemical industries leading to a decrease in its price. Therefore, production of a commercially valuable product from glycerol using an economically feasible process is desirable.[4]

Several chemicals can be derived from glycerol, including 1-2 and 1,3-propanediols, acrolein, acrylic acid, epichlorohydrin, 3-hydroxypropionic acid and other specialty chemicals. Among these chemicals, the production of 1,2- and 1,3-propanediol via glycerol hydrogenolyis has attracted significant commercial interest (FIG. 1). 1,2-Propandiol, also known as propylene glycol, is a major commodity chemical and has seen a 4% market growth every year.[4] Propylene glycol has several commercial applications, for example, as antifreeze, coolant, solvent and extractant, deicing agent, precursor in pharmaceuticals, cosmetics, animal food and tobacco industries, petroleum production, sugar refining, paper making, toiletries, liquid detergent, alkyl resins, printing inks, plasticizers, and hydraulic break fluids.[8,9,10]

Propylene glycol is currently produced from petroleum derivatives such as propylene oxide and chlorohydrin by chemical routes.[11,12,13] The sharp increase in oil price and the declining petroleum resource has made this route expensive. Therefore the production of propylene glycol from renewable resources such as glycerol has attracted much attention. Che et al.[14] used [Rh(CO)$_2$(acac)] and tungstenic acid as a homogeneous catalyst for hydrogenolysis of aqueous glycerol with syngas at 30 MPa and 200° C. and reported 20% and 30% yield of 1,3-propandiol and 1,2-propandiol, respectively. Drent and Jager[15] used a homogeneous palladium complex and methanesulfonic acid and reported 22% yield of propylene glycol. Schlaf et al.[16] used a homogeneous ruthenium complex as catalyst for dehydroxylation of glycerol in sulfolane at 5.2 MPa and 110° C. and obtained low yield of propylene glycol. Various heterogeneous catalysts, mainly Cu based mixed oxides and supported noble metals have been used for hydrogenolysis of glycerol. Cu is known to suppress C—C bond cleavage and for C—O bond breaking in glycerol to produce propylene glycol.[17,18] Mane et al.[19] prepared Cu—Al nanocatalysts by a simultaneous co-precipitation method and obtained 91% selectivity to propylene glycol at 220° C. and 7 MPa H$_2$ pressure in 5 h. Some papers also mentioned the use of bimetallic catalysts such as Cu/C, Cu—Pt, and Cu—Ru.[20,21] Roy et al.[1] studied the conversion of glycerol to propylene glycol using a mixture of 5 wt. % Ru/Al$_2$O$_3$ and 5 wt. % Pt/Al$_2$O$_3$ catalysts in varying amounts utilizing in situ generated hydrogen and reported 47.2% selectivity of propylene glycol at 50% conversion of glycerol. Schmidt et al.[22] used a Raney-Cu based catalyst in trickle bed mode and obtained 94% selectivity to propylene glycol and 100% glycerol conversion. Werpy et al.[23] reported glycerol hydrogenolysis over Ni/Re catalyst under 8.2 MPa H$_2$ and 230° C. in 4 h which led to 44% 1,2-propandiol yield. The use of organic supported catalysts, including carbon supported Ru, Pt, and bimetallic Pt—Ru and Al—Ru catalyst has also been reported.[24,25] Also, the Cu/ZnO based catalysts have been reported to give a high catalytic performance for the glycerol dehydroxylation reaction to propylene glycol under mild reaction conditions.[26,27] A Cu/Cr$_2$O$_3$ catalyst was reported to produce propylene glycol from glycerol.[28,29] Amberlyst-15 was used in addition with Ru to induce external acidity in the catalyst and an improvement in glycerol conversion was documented.[30,31] Vasiliadou and Lemonidou[4] reported that the total acidity of catalyst (induced either by support and/or by the metal precursor) strongly affects the glycerol conversion. It is reported that ZnO acts as a reservoir for atomic hydrogen and promotes hydrogen spillover for the reaction which can increase the activity of the catalyst.[32-33] Raju et al.[34] reported that a ZrO$_2$ based catalyst is responsible for acetol production from glycerol. Several reports support the acidic nature of ZrO$_2$.[35,36,37,38,39]

Despite the report of several investigations, the heterogeneous catalyzed glycerol hydrogenolysis process still has several drawbacks which limit its scale up to pilot plant level. These problems include the use of dilute glycerol solution (10-30%), high temperatures (300-350° C.), high pressures (10-30 MPa), poor catalyst reusability, catalyst leaching, lower glycerol conversion and/or lower propylene glycol selectivity. The selective hydrogenolysis of glycerol to propylene glycol requires the preferential cleavage, by hydrogen, of the C—O bond over the C—C bond in the glycerol molecule.[40]

SUMMARY OF THE APPLICATION

In the present application, a multicomponent catalyst based on Cu, Zn, Cr and Zr was prepared using a co-precipitation method and the catalyst was studied for glycerol hydrogenolysis to provide propylene glycol as the major product.

Accordingly the present application includes a process for the hydrogenolysis of glycerol to produce propylene glycol comprising:
(a) contacting the glycerol with hydrogen in the presence of a heterogeneous catalyst under conditions for the formation of propylene glycol; and
(b) optionally isolating the propylene glycol, wherein the heterogeneous catalyst comprises, consists essentially of or consists of Cu, Zn, Cr and Zr.

In an embodiment of the application the process provides, as the major product, propylene glycol.

The present application also includes a process for producing propylene glycol comprising:
(a) contacting glycerol with hydrogen in the presence of a heterogeneous catalyst under conditions for the formation of propylene glycol; and
(b) optionally isolating the propylene glycol, wherein the heterogeneous catalyst comprises, consists essentially of or consists of Cu, Zn, Cr and Zr.

The present application further includes a composition comprising a heterogeneous catalyst, glycerol, water and hydrogen gas, wherein the heterogeneous catalyst comprises, consists essentially of or consists of Cu, Zn, Cr and Zr.

Other features and advantages of the present application will become apparent from the following detailed description. It should be understood, however, that the detailed description and the specific examples while indicating embodiments of the application are given by way of illustration only, since various changes and modifications within the spirit and scope of the application will become apparent to those skilled in the art from this detailed description.

BRIEF DESCRIPTION OF THE DRAWINGS

The present application includes references to appended drawings in which.

DETAILED DESCRIPTION OF THE APPLICATION

I. Definitions

Figure 1:
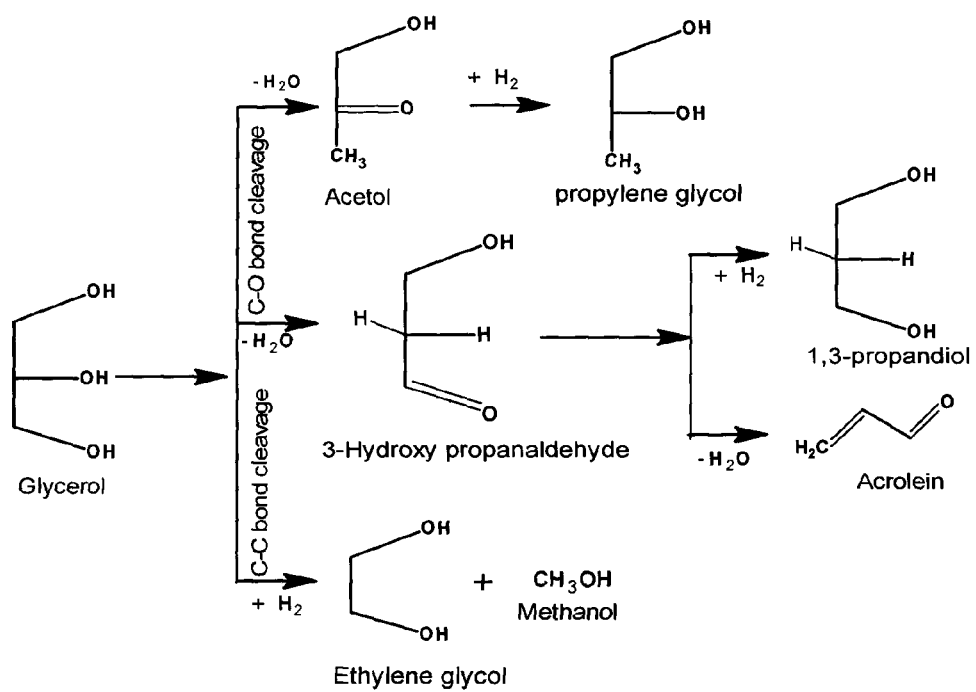
FIG. 1 is a schematic showing the major products of glycerol hydrogenolysis.

Unless otherwise indicated, the definitions and embodiments described in this and other sections are intended to be applicable to all embodiments and aspects of the application herein described for which they are suitable as would be understood by a person skilled in the art.

As used in this application, the singular forms "a", "an" and "the" include plural references unless the content clearly dictates otherwise. For example, an embodiment including "a reducing agent" should be understood to present certain aspects with one reducing agent, or two or more additional reducing agents.

In embodiments comprising an "additional" or "second" component, such as an additional or second reducing agent, the second component as used herein is chemically different from the other components or first component. A "third" component is different from the other, first, and second components, and further enumerated or "additional" components are similarly different.

The term "suitable" as used herein means that the selection of the particular compound or conditions would depend on the specific synthetic manipulation to be performed, and the identity of the molecule(s) to be transformed, but the selection would be well within the skill of a person trained in the art. All process/method steps described herein are to be conducted under conditions sufficient to provide the product shown. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps. For example, when a catalyst "consists essentially of" the stated elements, then only the stated elements are present for the purpose of catalysis, however the catalyst may include other elements that do not materially affect the basic function of the catalytic elements, and/or that do not function as part of the catalytic process.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The term "under conditions for the formation of propylene glycol" refers to the combination of hydrogenolysis reaction conditions under which glycerol is converted to propylene glycol as the major product. Specific conditions that can be varied would be known to a person skilled in the art and include, for example, amount of catalyst (or catalyst loading), hydrogen pressure, glycerol concentration, temperature, agitation speed, hydrogen flow rate and glycerol solution flow rate.

The term "major product" as used herein means that the stated product comprises greater than 50%, on a molar basis, of all of the products formed by the process. In an embodiment, the major product comprises greater than 80%, 85%, 90% or 95% of the products formed in the reaction process. In a further embodiment, the major product is formed with a selectivity of greater than 90%, 95%, 96%, 97%, or 98%, over all other products formed in the process.

The term "heterogeneous catalyst" as used herein refers to catalyst that is in a different form from that of the reactants. In the present application, the heterogeneous catalyst is a solid, where the reactants are gases and/or liquids.

II. Processes of the Application

A novel Cu:Zn:Cr:Zr catalyst with the elemental molar ratio 3:2:1:x (where x=1 to 4) was prepared and used for glycerol hydrogenolysis reaction to produce propylene glycol. It was observed that the introduction of zirconium metal increased the selectivity and conversion of the reaction. This process has distinctive competitive advantages over traditional processes, including, for example, the ability to use crude glycerol obtained from biodiesel process to produce propylene glycol in a high yield of 93%. The use of the pure glycerol resulted in a 97% yield of propylene glycol. The catalyst shows only a 10-15% decrease in activity even after four runs without affecting the selectivity of propylene glycol. XRD results of the Cu:Zn:Cr:Zr based catalyst confirmed the presence of active metallic Cu in the reduced catalyst. Continuous reactions were carried out in a trickle fixed bed catalytic reactor with an 80 wt % glycerol solution. The effects of temperature, hydrogen pressure, hydrogen flow rate, glycerol concentration, glycerol flow rate and catalyst pellet prepared with different loads applied were studied. At a temperature of 235° C., with a hydrogen pressure of 800 psi, a 15 mL catalyst bed, a hydrogen flow rate of 150 mL/min, a glycerol flow rate of 10 mL/h and an LHSV of 0.67 h$^{-1}$, the catalyst Cu:Zn:Cr:Zr with an elemental molar ratio of 3:2:1:3 was observed to give 99% glycerol conversion and 97% propylene glycol selectivity. The catalyst activity was evaluated for up to 200 hours and no decease in glycerol conversion and propylene glycol selectivity was found. Operation of a continuous reactor at a hydrogen flow rate of 1.50 L/min, a liquid glycerol solution feed flow rate of 0.40 mL/min, and an average reactor temperature of 233° C. 2° C. on a 120 mL catalyst reactor bed volume using the catalyst Cu:Zn:Car (3:2:1:3) was found to result in a glycerol conversion of 99% and a propylene glycol (PG) yield of 64%.

Accordingly the present application includes a process for the hydrogenolysis of glycerol to produce propylene glycol comprising:
(a) contacting the glycerol with hydrogen in the presence of a heterogeneous catalyst under conditions for the formation of propylene glycol; and
(b) optionally isolating the propylene glycol,
wherein the heterogeneous catalyst comprises, consists essentially of or consists of Cu, Zn, Cr and Zr.

In an embodiment, the propylene glycol is formed as the major product in the process. In an embodiment, the propylene glycol is formed with a selectivity of greater than 90%, 95%, 96%, 97%, or 98%.

In an embodiment, the heterogeneous catalyst is prepared using a co-precipitation method in which calculated amounts of suitable metal salts are dissolved in water, for example distilled water, at a temperature for their dissolution, for example about 50° C. to about 100° C., about 60° C. to about 80° C. or about 70° C. The catalyst is then precipitated by adjusting the pH of the dissolved metal solution to a value of about 8.5 to about 10.5 or about 9 to about 10. The pH is adjusted by addition of a suitable base, such as an alkali metal hydroxide or carbonate, or mixtures thereof. In an embodiment, the precipitate is aged prior to being filtered. In another embodiment, the aging is performed at a temperature of about 50° C. to about 90° C. or about 70° C. for a time of about 1 hour to about 10 hours or about 5 hours. The solid catalyst is then dried and calcined. In an embodiment, drying is performed in an oven at a temperature of about 100° C. to about 150° C., about 110° C. to about 130° C., or about 120° C. for about 6 hours to about 24 hours or about 12 hours. In another embodiment, calcination is performed by heating the dried catalyst at about 500° C. to about 800° C., about 600° C. to about 700° C., or about 650° C. for about 1 hour to about 12 hours, about 2 hours to about 5 hours, or about 3 hours. The elemental molar ratio of the metals in the heterogeneous catalysts is varied by varying the amount of metal salts used in the preparation method. In an embodiment the metal salts are nitrate salts.

The heterogeneous catalyst must be reduced for it to be active in the hydrogenolysis reaction. In an embodiment, reduction is affected by contacting the calcined catalyst with hydrogen, for example, at a temperature of about 200° C. to about 300° C., and a $H_2$ pressure of about 3 mPa to about 5 mPA for about 1 to about 3 hours. In another embodiment, the catalyst is reduced with a substantially continuous flow of hydrogen at a flow rate of about 0.05 L/min to about 0.5 L/min or about 0.15 L/min at a temperature of about 200° C. to about 350° C. or about 270° C. for about 1 hour to about 10 hours or about 5 hours. The reduction of the catalyst is either performed prior to the hydrogenolysis reaction or concurrently with the hydrogenolysis reaction.

In an embodiment, the heterogeneous catalyst comprises, consists essentially of or consists of Cu, Zn, Cr and Zr in an elemental molar ratio (Cu:Zn:Cr:Zr) of 3:2:1:1, 3:2:1:2, 3:2:1:3 or 3:2:1:4. In another embodiment, the heterogeneous catalyst comprises, consists essentially of or consists of Cu, Zn, Cr and Zr in an elemental molar ratio (Cu:Zn: Cr:Zr) of 3:2:1:3 or 3:2:1:4. In yet another embodiment, the heterogeneous catalyst comprises, consists essentially of or consists of Cu, Zn, Cr and Zr in an elemental molar ratio (Cu:Zn:Cr:Zr) of 3:2:1:3.

In an embodiment of the application, the glycerol used in the process is a solution, for example an aqueous solution, comprising at least about 50% (w/w) glycerol. In a further embodiment, the glycerol is an aqueous solution comprising about 60% (w/w) to about 90% (w/w), about 70% (w/w) to about 85% (w/w), or about 80% (w/w) glycerol. In another embodiment, the glycerol is an aqueous solution comprising about 60% (w/w) to about 90% (w/w), about 70% (w/w) to about 85% (w/w), about 80% (w/w) glycerol or about 70% (w/w) glycerol. It is a further embodiment that the glycerol is crude glycerol obtained as a byproduct from the production of biodiesel, that is from the $C_1$-$C_4$ alkyl alcohol alcoholysis of a glyceride. In a further embodiment, the crude glycerol from biodiesel production has a purity of about 85% to about 95%. In yet another embodiment, the crude glycerol from biodiesel production has a $C_1$-$C_4$ alkyl alcohol and water concentration of less than 20% (w/w), 15% (w/w), 10% (w/w) or 5% (w/w).

In an embodiment, the crude glycerol byproduct of a $C_1$-$C_4$ alkyl alcohol alcoholysis of a glyceride is obtained by first neutralizing a crude glycerol feedstock to achieve a pH between 5 and 12. The $C_1$-$C_4$ alkyl alcohol and water are separated from the crude glycerol feedstock such that the combined concentration of water and $C_1$-$C_4$ alkyl alcohols is less than about 20% (w/w), 15% (w/w), 10% (w/w) or 5% (w/w). The separated crude glycerol feed is then used in the process of the present application.

In another embodiment of the application, the conditions for the formation of propylene glycol comprise use of a catalyst loading (or catalyst amount) of about 1% (w/w) to about 5% (w/w), about 3% (w/w) to about 4% (w/w), or about 3% (w/w).

In another embodiment of the application, the conditions for the formation of propylene glycol comprise use of an $H_2$ pressure of about 1 MPa to about 10 MPa, about 2 MPa to about 6 MPa, or about 4 MPa. In a further embodiment, the conditions for the formation of propylene glycol comprise use of an $H_2$ pressure of about 1 MPa to about 10 MPa, about 2 MPa to about 6 MPa, about 4 MPa or about 5.5 MPa.

In another embodiment of the application, the conditions for the formation of propylene glycol comprise use of a temperature of about 150° C. to about 300° C., about 200° C. to about 250° C., or about 220° C. In another embodiment, the conditions for the formation of propylene glycol comprise use of a temperature of about 150° C. to about 300° C., about 200° C. to about 250° C., about 220° C. or about 235° C.

In another embodiment of the application, the conditions for the formation of propylene glycol comprise use of an agitation speed of about 500 rpm to about 1500 rpm, about 800 rpm to about 1400 rpm, about 900 rpm to about 1100 rpm, or about 1000 rpm.

In an embodiment, the heterogeneous catalyst is in pelletized form. In another embodiment, the heterogeneous catalyst is in powdered form.

It will be appreciated by a person skilled in the art that further conditions such as hydrogen flow rate and/or glycerol flow rate can also be varied. Such conditions may depend, for example, on the set-up and/or capabilities of the reactor. The selection of suitable conditions for a particular process of the application can be made by a person skilled in the art based on routine experimentation in light of their common general knowledge and with reference to the present application. For example, it would be appreciated by a person skilled in the art based on the present disclosure that increasing the hydrogen flow rate can result in an increase in the percent glycerol conversion and percent propylene glycol selectivity. It would also be appreciated by a person skilled in the art based on the present disclosure that increasing the glycerol flow rate above that which provides a useful residence time of glycerol can result in a decrease in catalyst activity.

The present application also includes a process for producing propylene glycol comprising:
(a) contacting glycerol with hydrogen in the presence of a heterogeneous catalyst under conditions for the formation of propylene glycol; and
(b) optionally isolating the propylene glycol,
wherein the heterogeneous catalyst comprises, consists essentially of or consists of Cu, Zn, Cr and Zr.

The processes of the present application allow the conversion of glycerol to propylene glycol with high selectivity.

Figure 9:
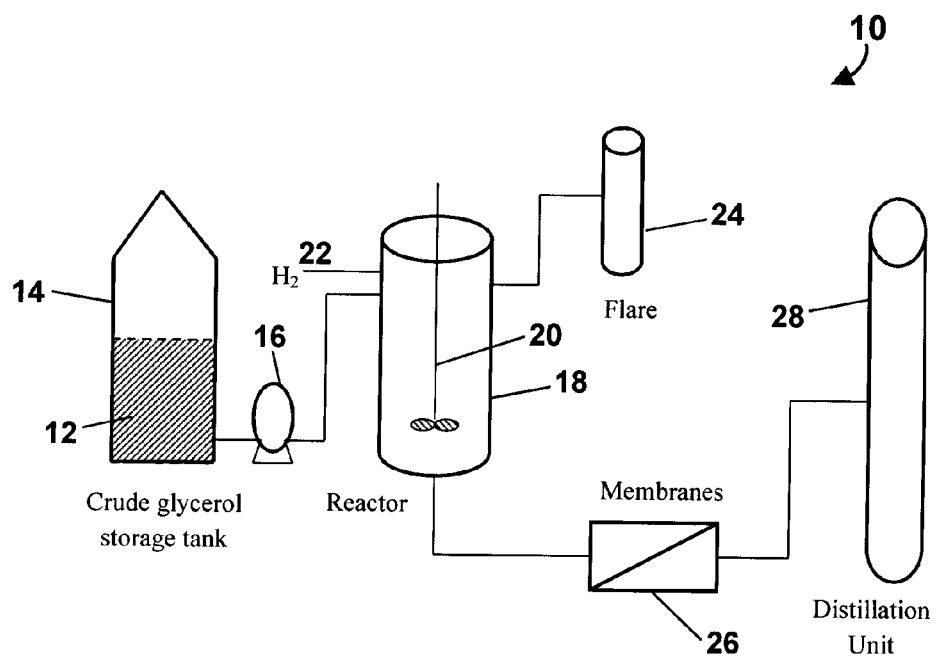
FIG. 9 is a schematic showing an exemplary embodiment of a continuous process flow set up for the hydrogenolysis of glycerol to propylene glycol using a catalyst of the application.

The processes of the application may be performed in a batch or continuous format. Commercial processes will generally be performed in a continuous format. An example of a continuous process set up is shown in FIG. 9. In the continuous format, a glycerol-containing process stream, for example from biodiesel production, is fed into a reactor that is equipped with an agitator, an inlet for $H_2$ gas and one or more outlets through which product and catalyst (for re-use) can be removed. It is an embodiment that the catalysts are reused or recycled at least 1, 2, 3, 4 or 5 times. It is a further embodiment that the product outlet leads to separation equipment which comprises one or more of separation membranes, distillation apparatuses or chromatography apparatuses.

III. Compositions of the Application

The present application also includes a composition comprising a heterogeneous catalyst, glycerol, water and hydrogen gas, wherein the heterogeneous catalyst comprises, consists essentially of or consists of Cu, Zn, Cr and Zr.

In an embodiment of the application, the heterogeneous catalyst comprises, consists essentially of or consists of Cu, Zn, Cr and Zr in an elemental molar ratio (Cu:Zn:Cr:Zr) of 3:2:1:1, 3:2:1:2, 3:2:1:3 or 3:2:1:4. In another embodiment, the heterogeneous catalyst comprises, consists essentially of or consists of Cu, Zn, Cr and Zr in an elemental molar ratio (Cu:Zn:Cr:Zr) of 3:2:1:3 or 3:2:1:4. In a further embodiment, the heterogeneous catalyst comprises, consists essentially of or consists of Cu, Zn, Cr and Zr in an elemental molar ratio (Cu:Zn:Cr:Zr) of 3:2:1:3.

The following non-limiting examples are illustrative of the present application:

EXAMPLES

Chemicals and Gases

Examples 1-3

The following chemicals were procured from VWR, Canada and used without further purification: glycerol, copper (II) nitrate trihydrate, zinc (II) nitrate hexahydrate, chromium nitratenonahydrate, zirconium nitrate, potassium carbonate, ethylene glycol, acetol, and propylene glycol. Hydrogen, helium, nitrogen, and air (HP grade, 99.99% purity) were also used in this work.

Example 1

Catalyst Synthesis

Catalysts were prepared using the co-precipitation method. Calculated amounts of copper nitrate $(Cu(NO_3)_2.3H_2O$, 23 g), chromium nitrate $(Cr(NO_3)_2.9H_2O$, 15.4 g), zinc nitrate $(Zn(NO_3)_2.6H_2O$, 18.2 g) and zirconium nitrate $(Zr(NO_3)_2.XH_2O$, 15.3 g) were dissolved in 1 L distilled water at 70±2° C. A solid was precipitated by addition of a 1M solution of potassium carbonate until the pH reached 9-10 with continuous stirring. The precipitate was aged further at 70±2° C. for 5 h. After cooling, the precipitate was filtered and washed thoroughly with distilled water until the pH became neutral. The solid cake was dried at 120±5° C. for 12 h in oven. Finally, the solid material was calcined at 650±10° C. for 3 h to produce a catalyst with elemental molar ratio Cu:Zn:Cr:Zr of 3:2:1:3. The other catalysts were prepared using the same method by varying the amount of chemicals.

Example 2

Experimental Setup and Reaction Procedure for Testing Catalysts

Experiments were carried out in a 300 ml stainless steel Parr autoclave. A four-bladed pitch turbine impeller was used for stirring. A calculated quantity of the catalyst was reduced at 250° C. and 4 MPa $H_2$ pressure for 2 h. The reactor was then cooled to room temperature and hydrogen gas was released and a known quantity of reactant (glycerol) was charged into the autoclave and the reactor was initially flushed with nitrogen gas. Then the reactor was pressurized with $H_2$ gas to the desired pressure. The temperature was raised to the set value and agitation was started. The total pressure was higher than set value because of autogenous pressure. Samples were withdrawn at regular intervals of 1 h. Additional hydrogen was added to maintain the original pressure as the reaction proceeded. A standard reaction was carried out for up to 10 h with 100 g of glycerol solution (80%), catalyst loading of 3% w/w, $H_2$ pressure of 4 MPa, agitation speed of 1000 rpm and temperature of 240° C.

Example 3

Method of Analysis

A gas chromatograph (Agilent 7890A) with flame ionizing detector (FED) was used for analyzing the primary and polyhydric alcohol and residual glycerol present in the sample. A stabilwax capillary column, with 30 m length and 0.25 mm inside diameter with 0.5 μm film thickness was used for analysis. A 0.1 g of sample was mixed with 0.2 ml of external standard (l-butanol) and deionized water was added to make up to 1.5 ml of solution. The oven temperature was set at 100° C. for 2 min and ramped to 280° C. at 10° C./min with the final hold time of 5 min. 1 mL of the sample was injected with the split ratio 10:1. Helium was used as the carrier gas. All experiments were performed in duplication and had an error of ±5%. The products were confirmed by GC-MS. Glycerol conversion and selectivity was calculated as follows:

$$\text{Conversion (\%)} = \frac{\text{(Initial moles of glycerol} - \text{final moles of glycerol)}}{\text{Initial moles of glycerol}} \times 100 \quad (1)$$

$$\text{Selectivity of a product (\%)} = \frac{\text{Moles of product formed}}{\text{Total moles of all products formed}} \times 100 \quad (2)$$

Results and Discussion for Examples 1-3

Catalysts Screening

The acid-catalyzed mechanism for glycerol hydrogenolysis proceeds by a C—O bond breaking step that involves dehydration followed by hydrogenation (FIG. 1). Dehydration of glycerol results in acetol formation and further hydrogenation gives propylene glycol. In the present work, incorporation of zirconia renders the catalyst acidic so that the reaction proceeds via the acid catalysis route. This was confirmed by formation of acetol during the reaction. The catalyst Cu:Zn:Cr:Zr with elemental molar ratio 3:2:1:3 produced 1,2-propandiol as a major product and acetol as minor product.

Various catalysts were screened to assess their efficacy for hydrogenolysis of glycerol to propylene glycol. Reaction conditions comprised 100 g of glycerol solution (80%), catalyst loading of 3% w/w, hydrogen pressure of 4 MPa and temperature of 240° C. The catalysts with the elemental molar ratio Cu:Zn:Ni (3:2:2), Cu:Cr:Ni (3:1:2), Cu:Zn:Cr (3:2:1), Cu:Zn:Cr:Ni (3:2:1:2), Cu:Zn:Cr:Zr (3:4:1:3) and Cu:Zn:Cr:Zr (3:2:1:3) were prepared according to the method described in Example 1 and screened using the methods described in Examples 2 and 3. The catalyst with elemental molar ratio Cu:Zn:Cr:Zr (3:2:1:3) showed the highest glycerol conversion and propylene glycol selectivity (see Table 1). Further experiments were conducted with Cu:Zn:Cr:Zr (3:2:1:3) to assess the effect of other variables of the reaction.

Effect of Zirconium Loading

The catalysts with different elemental molar ratio of zirconium such as Cu:Zn:Cr:Zr (3:2:1:1) Cat-A, Cu:Zn:Cr:Zr (3:2:1:2) Cat-B, Cu:Zn:Cr:Zr (3:2:1:3) Cat-C and Cu:Zn:Cr:Zr (3:2:1:4) Cat-D were prepared and the effects of Zr loading on the glycerol hydrogenolysis reaction is reported in Table 2. It was observed that with increasing zirconium loading from Cat-A to Cat-D in the catalyst matrix, conversion was increased but after Cat-C the propylene glycol selectivity was decreased. While not wishing to be limited by theory, this may be explained by the increased acidity in the catalyst with increasing amounts of Zr. Cat-D has higher acidity compared to Cat-C and leads to the formation of parallel side products, such as acrolein, acetaldehyde, 1,3-propanediol and ethylene glycol which decrease the selectivity for propylene glycol.

Figure 2:
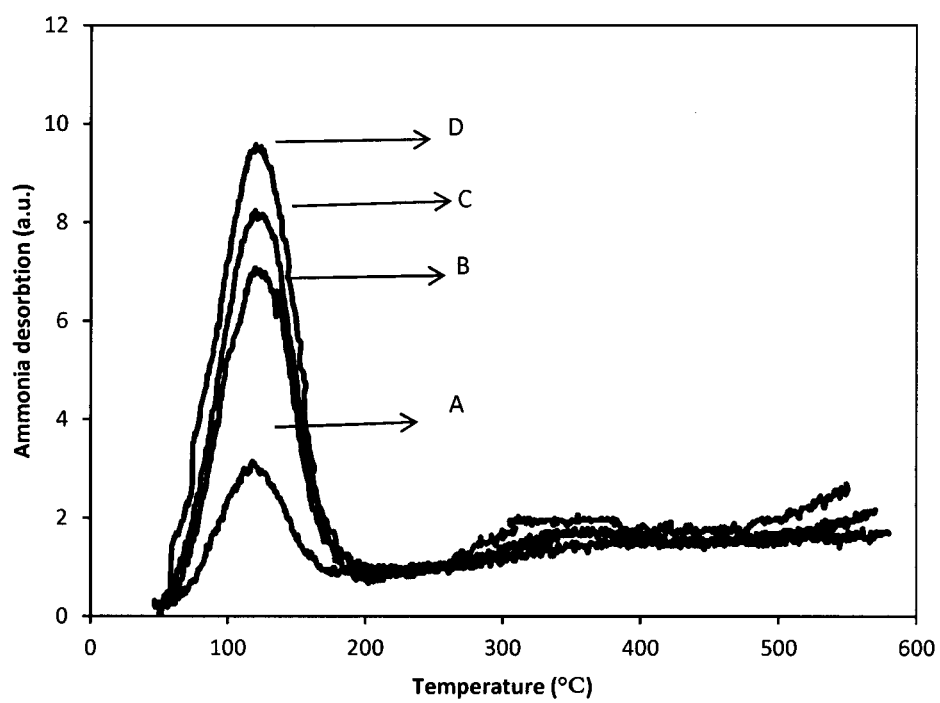
FIG. 2 is a graph showing the $NH_3$-TPD profile: i) A is Cu:Zn:Cr:Zr with elemental molar ratio 3:2:1:1, ii) B is Cu:Zn:Cr:Zr with elemental molar ratio 3:2:1:2, iii) C is Cu:Zn:Cr:Zr with elemental molar ratio 3:2:1:3 and iv) D is Cu:Zn:Cr:Zr with elemental molar ratio 3:2:1:4.

Acidic strength of the catalysts was studied by $NH_3$-TPD ($NH_3$-Temperature Programmed Desorption) (FIG. 2). Ammonia acts as a suitable probe molecule due to its small size and basicity, which interacts with the acid sites present in the catalyst. The temperature range in which ammonia desorbed is an indicator of the strength of the acid sites. $NH_3$-TPD profile of the catalysts displayed that most of the ammonia was desorbed in the range of 100-120° C. that represented weak Bronsted acid sites. It can also be concluded from $NH_3$-TPD profile that with an increase in zirconia content in the catalyst the acidity also increased. Hence, a catalyst with a Cu:Zn:Cr:Zr ratio of 3:2:1:3 was used for further studies.

Optimization Study in Batch Reactor (a) Effect of Speed of Agitation

Figure 3:
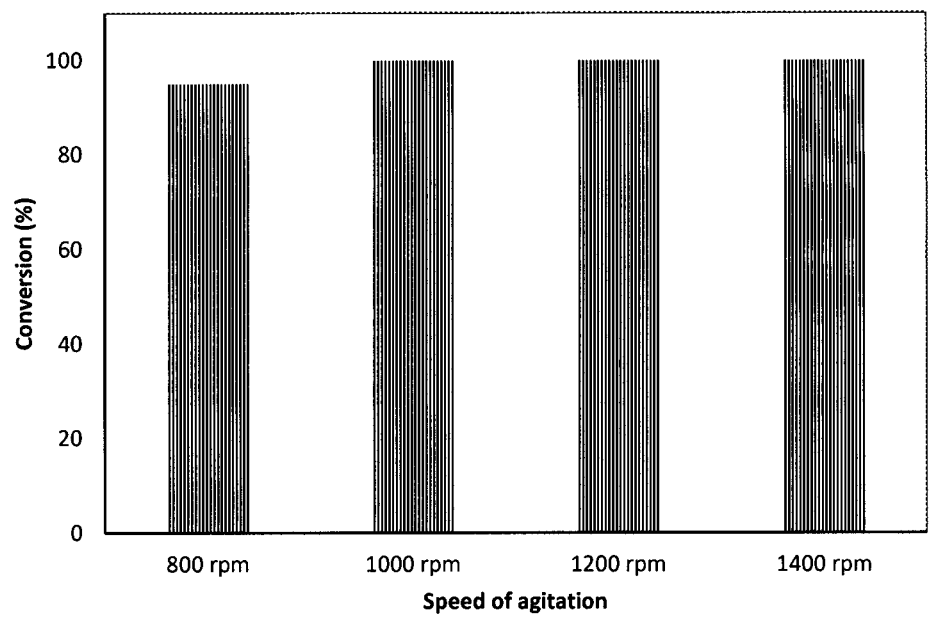
FIG. 3 is a bar graph showing the effect of speed of agitation: 100 g of glycerol solution (80%), catalyst of 3% w/w, $H_2$ pressure of 4 MPa, temperature of 240° C., 10 h.
Figure 4:
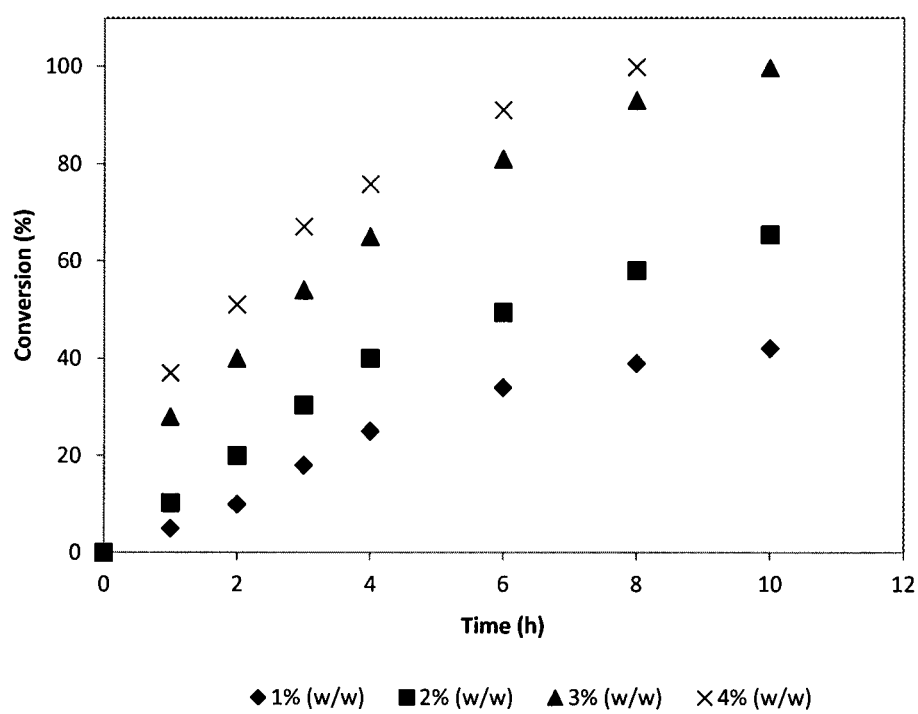
FIG. 4 is a graph showing the effect of catalyst loading: 100 g of glycerol solution (80%), $H_2$ pressure of 4 MPa, agitation speed of 1000 rpm, temperature of 240° C., 10 h.
Figure 5:
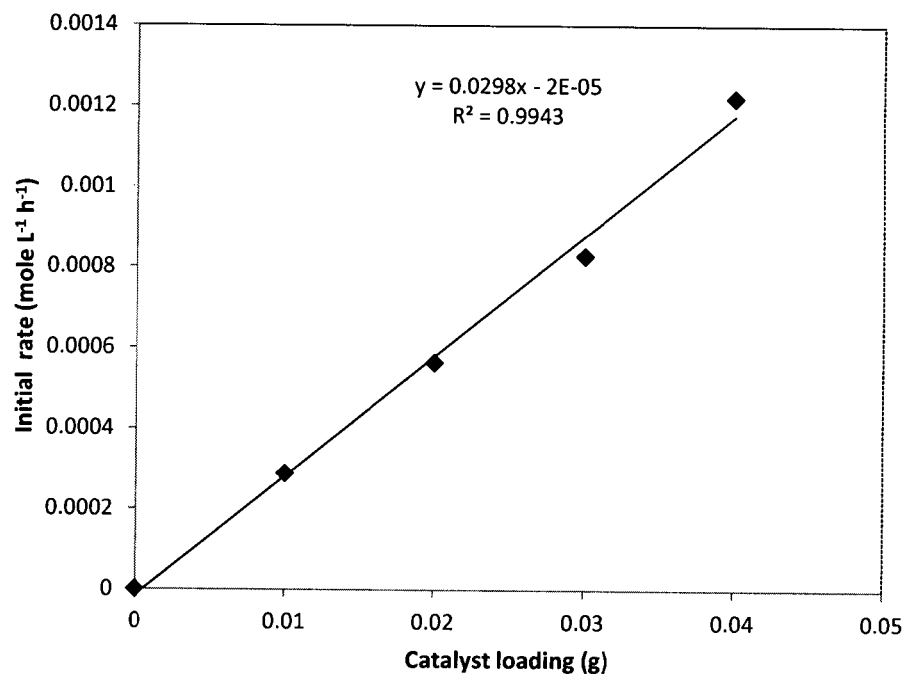
FIG. 5 is a graph showing the initial rate (mole$^{-1}$ min$^{-1}$) vs catalyst loading (g): 100 g of glycerol solution (80%), $H_2$ pressure of 4 MPa, agitation speed of 1000 rpm, temperature of 240° C., 10 h.

External mass transfer resistance between the bulk liquid phase and catalyst surface was evaluated by varying the speed of agitation in the range of 800-1400 rpm under otherwise similar reaction conditions (100 g of glycerol solution (80%), 3% w/w of catalyst, 4 MPa of $H_2$ pressure, 240° C. of temperature, 10 h). The conversion of the glycerol was found to decrease to some extent for stirring below 1000 rpm (FIG. 3). There was no external mass transfer resistance on the overall rate of reaction at or beyond 1000 rpm. Such high stirring speed was suitable due to the viscous nature of the feedstock. Thus, the speed of agitation was kept as 1000 rpm for the further experiments to assess the effect of other variables on reaction (b) Effect of Catalyst Loading The catalyst amount was varied in the range of 1 to 4% w/w. The conversion was found linear with catalyst loading (FIG. 4). While not wishing to be limited by theory, this is likely due to the proportional increase in the active site of the catalyst. The initial rate of reaction also increased linearly with catalyst loading (FIG. 5). Further, reactions were carried out with 3% w/w of catalyst loading. The selectivity towards propylene glycol remained 97±2% in all cases.

(c) Effect of Hydrogen Pressure

Figure 6:
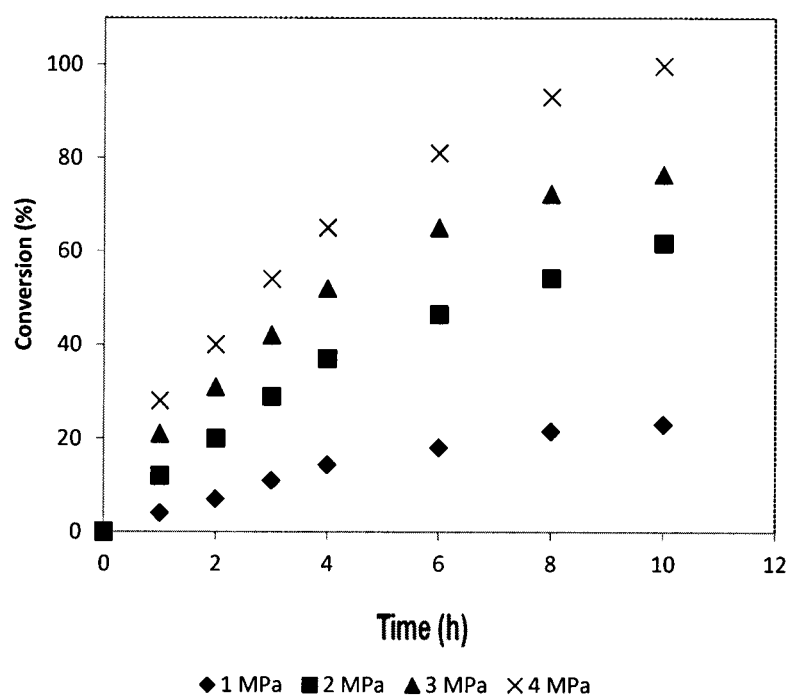
FIG. 6 is a graph showing the effect of hydrogen pressure: 100 g of glycerol solution (80%), catalyst of 3% w/w, agitation speed of 1000 rpm, temperature of 240° C., 10 h.

This study included the effects of hydrogen partial pressure on the conversion and selectivity pattern of the reaction. The reactor was pressurized in the range of 1 to 4 MPa by hydrogen gas. It was observed that autogeneous pressure was generated at 240° C. Hence, total pressure of the reaction lies in the range of 2 to 6.5 MPa of hydrogen. It was observed that with increasing the hydrogen pressure the conversion of glycerol also increased (FIG. 6). While not wishing to be limited by theory, this is likely due to a higher solubility of hydrogen in the reaction mixture with increasing hydrogen pressure. The increased hydrogen pressure showed no effect on the selectivity of propylene glycol and it was 97±2%. While not wishing to be limited by theory, this is likely because no further reaction of 1,2-propanediol takes place at a higher pressure of hydrogen. Further experiments were carried out at 4 MPa of hydrogen pressure.

(d) Effect of Glycerol Concentration

Figure 7:
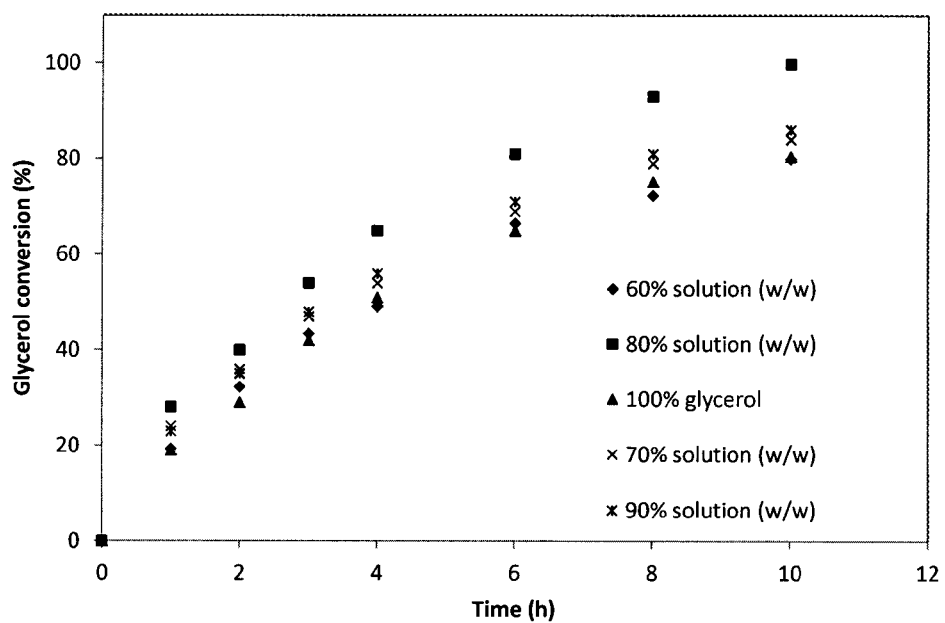
FIG. 7 is a graph showing the effect of glycerol concentration: 100 g of glycerol solution, catalyst of 3% w/w, $H_2$ pressure of 4 MPa, agitation speed of 1000 rpm, temperature of 240° C., 10 h.

The effect of glycerol concentration (60 to 100%) in the solution on hydrogenolysis reaction was studied (FIG. 7). It was observed that with an increase in glycerol concentration from 80 to 100% and for a fixed amount of catalyst loading, the conversion of glycerol decreased. While not wishing to be limited by theory, this is likely because of two factors: i) viscosity of the solution was increased and ii) catalyst to glycerol ratio was decreased. Hence, smaller numbers of active sites were available to convert the glycerol to propylene glycol and higher glycerol concentrations. In the case of 60 and 70% glycerol solution, it is likely that the decrease in conversion was due to the presence of more water in the reaction solution that made the catalyst less active. Propylene glycol selectivity was found to be 97±2% for all glycerol concentrations. Further, experiments were carried out by using 80% (w/w) glycerol solution.

(e) Effect of Temperature

Figure 8:
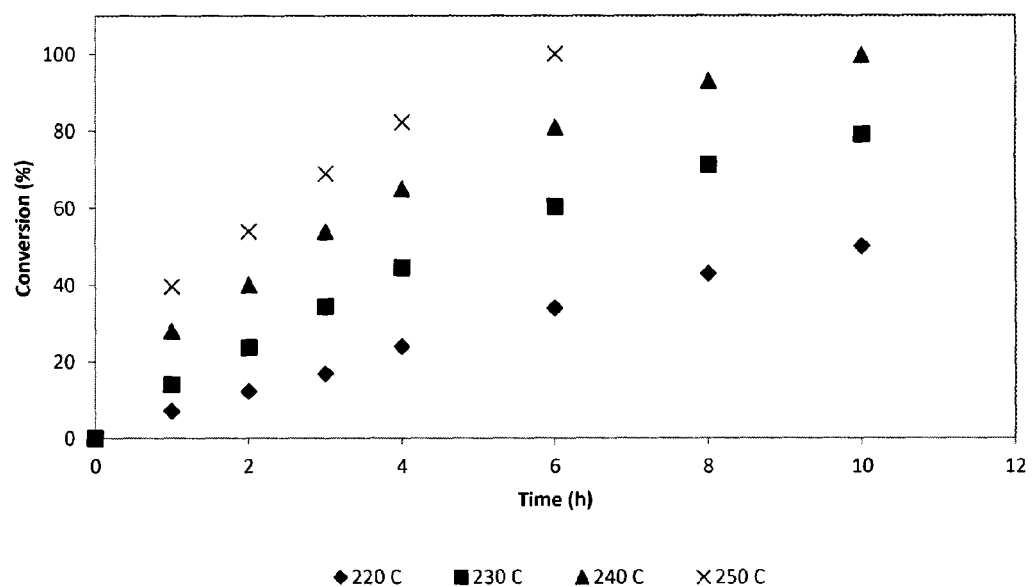
FIG. 8 is a graph showing the effect of temperature: 100 g of glycerol solution (80%), catalyst 3% of w/w, $H_2$ pressure of 4 MPa, agitation speed of 1000 rpm, 10 h.

The effect of temperature was studied in the range of 220 to 250° C. (FIG. 8). During the experiments, samples were withdrawn periodically and after each sample the total pressure of the reaction was maintained at 6 MPa. Glycerol conversion increased with temperature. The selectivity of the propylene glycol was not affected with increase in the temperature.

(g) Propylene Glycol from Crude Glycerol

Crude glycerol was obtained from a biodiesel experiment and had a purity of 90%. Hydrogenolysis of the crude glycerol was carried out to obtain propylene glycol under the optimized reaction conditions (i.e. glycerol solution (80%), 3% w/w of catalyst, 4 MPa of $H_2$ pressure, 250° C.). It was observed that the crude glycerol reaction took longer for complete conversion as compared with pure glycerol. This may be due to the presence of impurities in the crude glycerol. However, there was no additional impurity observed after the reaction. The glycerol conversion was found to be 99% and selectivity was 93%. Hence, it can be concluded that the novel catalyst Cu(3):Zn(2):Cr(1):Zr(3) can also be used for crude glycerol obtained from the biodiesel industry to produce propylene glycol in good yield and selectivity.

(g) Catalyst Reusability

The reusability of the catalyst was tested by conducting four runs (Table 3). After each reaction, the catalyst was filtered. Further, it was calcined at 650° C. for 3 h to remove adsorbed reactant and products from the active site of the catalyst. The actual amount of catalyst used in the next batch, was almost 5% less than the previous batch. The loss of the catalyst was made up with fresh catalyst. The conversion profiles gave a 10-15% decrease and the selectivity of propylene glycol was 97±2%. Hence, catalyst was found to be reusable.

Example 4

Large Scale Production of Catalyst and Batch Conversion of Glycerol to Propylene Glycol (a) Chemicals Used for Catalyst Preparation Sodium hydroxide (869.5 kg), copper (II) nitrate (1000 kg), zinc nitrate (791.3 kg), chromium(III) nitrate nonahydrate (669.5 kg), zirconium(IV) oxynitrate hydrate (665.2 kg) and distilled water (15,000 kg).

(b) Catalyst Preparation

Calculated amounts of copper nitrate ($Cu(NO_3)_2.3H_2O$), chromium nitrate $Cr(NO_3)_2.9H_2O$, zinc nitrate ($Zn(NO_3)_2.6H_2O$ and zirconium nitrate ($Zr(NO_3)_2.XH_2O$) were dissolved in 8000 kg of distilled water at 70±2° C. The solution was precipitated with sodium hydroxide (1M) solution until the pH reached 9-10 with continuous stirring. The reaction mixture was cooled, and filtered through filter paper, and washed thoroughly with the distilled water till pH became neutral. The solid cake was dried at 120±5° C. for 12 h in oven. Finally, solid material was calcined at 650±10° C. for 3 h to obtain 1000 kg of catalyst.

(c) Chemicals Used for Hydrogenolysis Reaction

Crude glycerol (1509.4 kg) was obtained from biodiesel by-products and showed to be 90% pure by GC. Water (377.3 kg) was used as is and industrial grade hydrogen (32.63 kg) and nitrogen gas were obtained from Praxair.

(d) Hydrogenolysis Reaction Conditions

Crude glycerol solution: 1886.7 kg (80% w/w crude glycerol solution); Catalyst: 56.6 kg; Temperature: 250° C.; Hydrogen pressure: 4.0 MPa; Speed of agitation: 1000 rpm; Reaction time: 17 h (e) Hydrogenolysis Reaction Procedure An experiment was carried out in a 2.5 kiloliter stainless steel reactor. A four bladed pitch turbine impeller was used for stirring. Prior to the reaction, 56.6 kg of the catalyst was reduced at 250° C. with 4 MPa of $H_2$ pressure for 2 h. 1886.7 kg of crude glycerol solution (80% w/w) was placed into the reactor and the reactor was initially flushed with nitrogen gas. Then, it was pressurized up to 4.0 MPa with $H_2$ gas. The temperature was raised to 250° C. and agitation was started. The total pressure of the reactor reached up to 6.7 MPa due to autogenous pressure of the solution. The $H_2$ pressure was maintained constant to 6.7 MPa by pressuring it with additional hydrogen gas as needed. Approximately 10 g of sample was withdrawn after 17 h, and analyzed by gas chromatography to observe the progress of the reaction. (Percentage conversion and percentage selectivity should be 99% and 93% respectively). Then, the reaction was stopped.

(f) Product Isolation Procedure 50 kg of methanol was added to the reaction mixture to reduce the viscosity of the solution. The reaction mixture was filtered through filter paper, and further catalyst was washed with 50 kg of methanol. Filtered catalyst was dried in the oven at 100° C. for 2 h (Catalyst recovery was 93%). Methanol and water were distilled out from the filtrate to obtain propylene glycol. The weight of propylene glycol obtained was 1000 kg (i.e. 89% isolated yield). The purity of propylene glycol was measured by gas chromatography (92%), and had moisture content of <1%. Use of high vacuum fractional distillation increased the purity of 1,2-propanediol to 93.3% and the other impurities are in 4.0 and 2.6%.

Example 5

Continuous Process

The conversion of glycerol to propylene glycol using a catalyst of the present application may also be performed using a continuous process, for example using the process set up 10 shown in FIG. 9. For example, in one embodiment, crude glycerol 12, such as crude glycerol that is a byproduct from biodiesel production, is stored in a tank 14. The required amount of the crude glycerol 12 is pumped 16 from the storage tank 14 to a reactor 18. The reactor is optionally equipped with an agitator 20 and typically has at least one inlet for an $H_2$ gas stream 22 as well as one or more outlets through which product and/or catalyst (for example, for re-use of the catalyst) can be removed. The catalyst is added to the reactor 18 and the contents heated, for example, to about 200° C. to about 300° C., about 250° C. or about 235° C. The reactor 18 pressure is maintained by sparging $H_2$. Any unreacted $H_2$ gas in the reactor 18 is burned in a flare system 24. The reactor 18 contents are cooled and passed through membranes 26 to separate out the catalyst. The used catalyst From the process is stored for disposal to a land fill. The propylene glycol is separated from any unreacted glycerol and distilled to the required purity in a distillation unit 28.

Example 6

Further Studies of Cu:Zn:Cr:Zr Catalyst

An objective of the present work was to prepare and study the multi component catalyst Cu:Zn:Cr:Zr (3:2:1:3) in a selective glycerol hydrogenolysis reaction to obtain propylene glycol. The effect of various operating conditions such as temperature, hydrogen pressure, hydrogen flow rate and glycerol concentration on glycerol conversion and propylene glycol yield were studied. A trial for a scaled-up propylene glycol process with a 100 mL catalyst bed size was conducted using a fixed bed reaction system.

I. Experimental Section

Chemicals and Gases

The following chemicals were purchased and used without further purification: Glycerol (reagent grade, 99% purity from VWR, Canada), copper (II) nitrate trihydrate (purity ≥99% from VWR, Canada), zinc (II) nitrate hexahydrate (reagent grade, 98% purity from VWR, Canada), chromium nitrate nonahydrate (reagent grade ≥98% purity, from VWR, Canada), zirconium nitrate (reagent grade ≥98% purity, from VWR, Canada), potassium carbonate (lab grade ≥98% from VWR, Canada), 1,2-propandiol (reagent grade ≥99% purity from VWR, Canada) and 1-butanol (reagent grade ≥99% purity from Sigma-Aldrich). Hydrogen, helium, nitrogen and air with high purity grade, 99.99% were purchased from Praxair, Saskatoon, Canada.

Catalyst Synthesis

A co-precipitation method was used to prepare the catalysts with different elemental molar ratios. Copper nitrate $(Cu(NO_3)_2 \cdot 3H_2O$, 23 g), chromium nitrate $(Cr(NO_3)_2 \cdot 9H_2O$, 15.4 g), zinc nitrate $(Zn(NO_3)_2 \cdot 6H_2O$, 18.2 g) and zirconium nitrate $(Zr(NO_3)_2 \cdot xH_2O$, 15.3 g) were dissolved in 1000 mL of distilled water. The solution was precipitated with 1M solution of potassium carbonate with continuous vigorous stirring. Potassium carbonate solution was added until the pH of the solution reached in the range of 9-10. The precipitate was aged at 70±2° C. for 5 h. The reaction mixture was cooled to 25±2° C., the precipitate was filtered and washed thoroughly with distilled water until the pH reached 7.0. The solid cake was dried at 120±2° C. for 12 h in an oven. Finally, the solid material was calcined at 650±10° C. for 3 h to provide the catalyst Cu:Zn:Cr:Zr (3:2:1:3), (elemental molar ratios are presented in parenthesis)[41].

Experimental Setup and Reaction Procedure

Glycerol hydrogenolysis reactions were performed in a trickle bed catalytic reactor. The high pressure reaction set up used in this study simulates the process that takes place in industrial hydrotreaters. The system is made up of liquid and gas feeding sections, a high pressure reactor, a heater with a temperature controller for precisely controlling the temperature of the catalyst bed, a scrubber and a gas-liquid separator. The length and internal diameter of the reactor were 240 mm and 14 mm, respectively. Typically, the catalyst bed was 15 cm long and rest of the reactor volume was packed with silicon carbide. Nitrogen gas was passed with a rate of 15 mL/min for 30 min at room temperature to replace the air, then the catalyst was reduced with a continuous flow of hydrogen (0.15 L/min) at 270° C. for 5 h. Thereafter, hydrogen pressure was increased to 800 psi through the back pressure regulator and flow was maintained at 150 mL/min through the hydrogen mass flow controller. Glycerol solution (80% w/w) was fed with a flow rate of 10 mL/h through a high pressure liquid pump. Approximately 1 g of sample was collected after 24 h and analyzed by gas chromatography to monitor the progress of the reaction.

Method of Analysis

A gas chromatograph (Agilent 7890A) with a flame ionizing detector (FID) was used for analyzing the primary and polyhydric alcohol, and residual glycerol present in the sample. The stabilwax capillary column with a 30 m length and a 0.25 mm inner diameter with a 0.5 μm film thickness was used. 0.1 g of the sample was mixed with 0.02 mL of external standard (1-butanol) and deionized water was added to make up to 1.5 mL of the solution. The oven temperature was programmed to begin at 100° C. for 2 min and ramped to 240° C. at 10° C./min with a final hold time of 4 min. One microliter of the sample was injected into the column with a split ratio of 10:1. Helium was used as a carrier gas. The results have an error of ±3% throughout the experiments. The formation of propylene glycol was confirmed by GC-MS, $^1H$ NMR and $^{13}C$ NMR. Eqs. (1)-(3) were used to calculate conversion, product selectivity and yield, respectively.

$$\text{Conversion (\%)} = \frac{(\text{Initial moles of glycerol} - \text{final moles of glycerol})}{\text{Initial moles of glycerol}} \times 100 \quad (1)$$

$$\text{Selectivity of a product (\%)} = \frac{\text{percentage amount of product formed}}{\text{The total percentage product formed}} \times 100 \quad (2)$$

$$\text{Yield (\%)} = \quad (3)$$
$$(\% \text{ Conversion of glycerol} \times \% \text{ selectivity of desired product})/100$$

II. Results and Discussion

Catalyst Characterization

Figure 10:
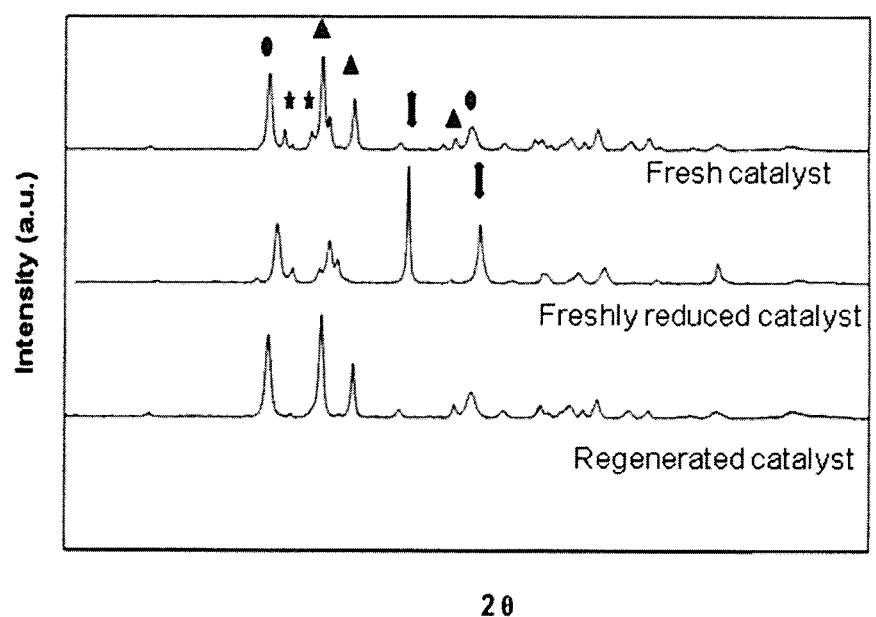
FIG. 10 shows exemplary X-Ray Diffraction (XRD) patterns of fresh (top), freshly reduced (middle) and regenerated (bottom) Cu:Zn:Cr:Zr (3:2:1:3) catalyst (Δ=CuO, O=$ZrO_2$, ☆=ZnO, and ⇧=Cu).

The brownish black color Cu:Zn:Cr:Zr catalyst powder was obtained after calcination at 650° C. for 3 h. In brief, the XRD patterns for the fresh, freshly reduced, and regenerated Cu:Zn:Cr:Zr (3:2:1:3) catalysts are presented in FIG. 10. The presence of the peaks at 2θ=35°, 38° and 47° [ICDD no. 00-048-1548] corresponds to CuO, peaks at 2θ=29° and 49° to $ZrO_2$ [ICDD no. 00-050-1089], peaks at 2θ=31°, 34° to ZnO [ICDD no. 01-070-8070], and peaks at 44° and 51° to Cu [ICDD no. 01-070-3038]. The intense peak observed at 2θ=44° in the XRD corresponds to metallic Cu which is present in the freshly reduced catalyst but is absent in the regenerated catalyst indicating that metallic Cu is converted into CuO after calcination at 650° C. The crystalline size of metallic Cu was found to be 16.9 nm by the Scherrer equation.

Figure 11:
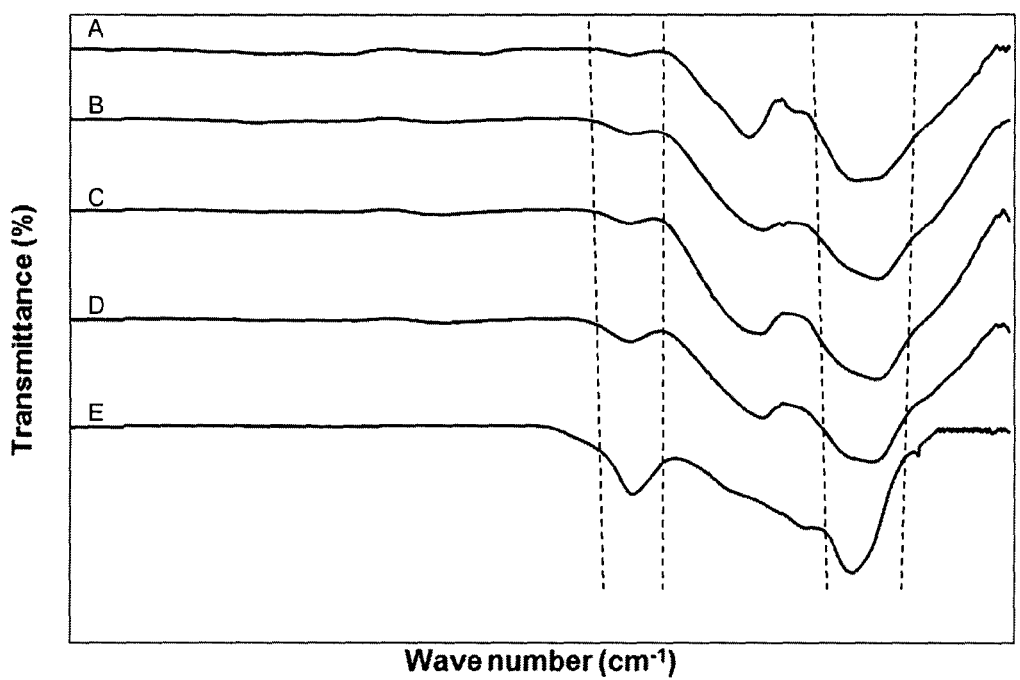
FIG. 11 shows exemplary FTIR spectra of (A) Cu:Zn:Cr:Zr (3:2:1:1), (B) Cu:Zn:Cr:Zr (3:2:1:2), (C) Cu:Zn:Cr:Zr (3:2:1:3), (D) Cu:Zn:Cr:Zr (3:2:1:4), and (E) $ZrO_2$.

The FTIR spectra of pure $ZrO_2$ and Cu:Zn:Cr:Zr (3:2:1:x) where x=1, 2, 3, 4 are shown in FIG. 11. The IR bands observed between 720-770 and 575-560 $cm^{-1}$ are the characteristic peaks of crystalline zirconia.[42,43] The presence of crystalline zirconia in the catalysts was also observed from the XRD data. The intensity of the IR band between 720-770 and 575-560 $cm^{-1}$ was found to increase from A to D due to an increase in the zirconia content in the catalyst.

Figure 12:
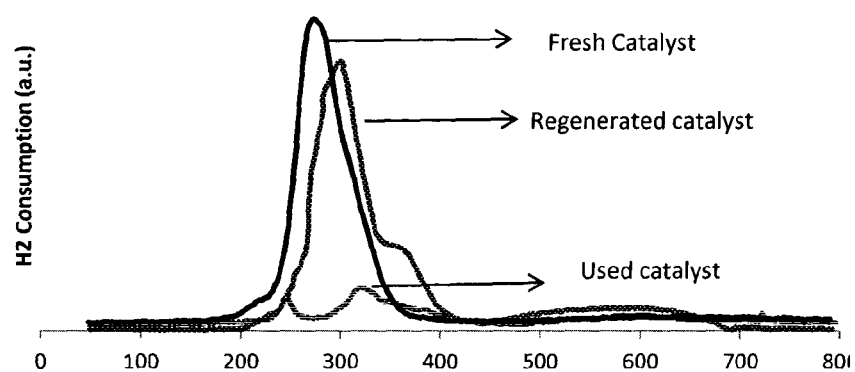
FIG. 12 shows an exemplary Temperature Programmed Reduction (TPR) profile of fresh catalyst (dark grey), regenerated catalyst (medium grey) and used catalyst (light grey).

Temperature programmed reduction (TPR) of fresh, freshly reduced and regenerated Cu:Zn:Cr:Zr (3:2:1:3) catalyst was carried out by using hydrogen as probe molecule (FIG. 12). A single peak observed in the range of 200-400° C. for the fresh catalyst was due to the hydrogen consumption for the reduction of copper oxide to metallic copper which was in accordance with a literature report.[44] The TPR profile of the freshly reduced catalyst did not show any peak at 200-400° C. which confirms the presence of only metallic Cu in the catalyst. The TPR profile of the regenerated catalyst shows a peak at 200-420° C. which is due to the presence of CuO.[41] The presence of metallic copper in freshly reduced catalyst was also confirmed by the XRD data.

Figure 13:
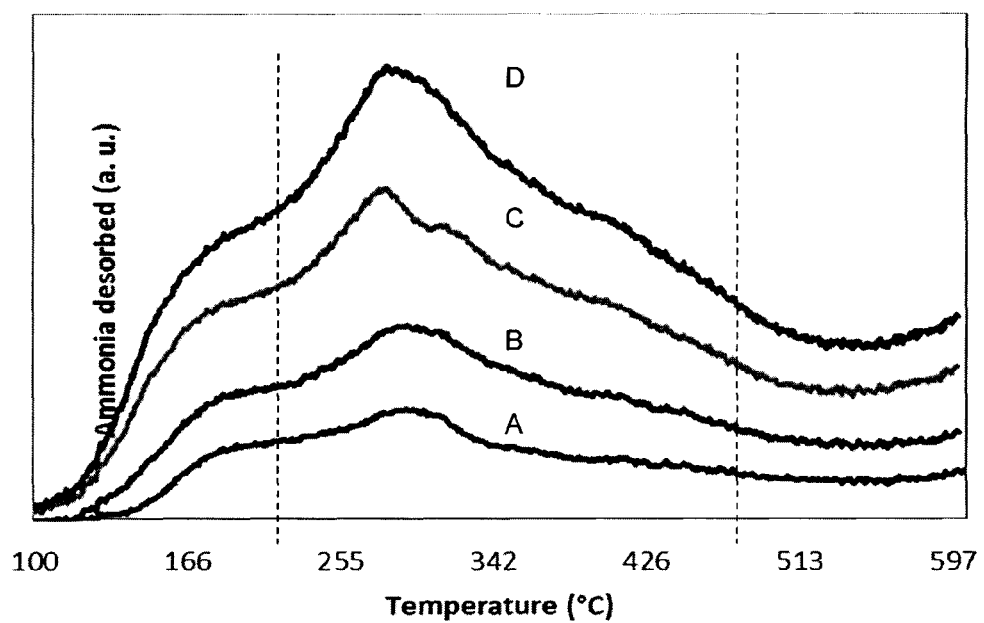
FIG. 13 shows an exemplary $NH_3$-TPD ($NH_3$-Temperature Programmed Desorption) profile of catalysts (A) Cu:Zn:Cr:Zr (3:2:1:1), (B) Cu:Zn:Cr:Zr (3:2:1:2), (C) Cu:Zn:Cr:Zr (3:2:1:3), and (D) Cu:Zn:Cr:Zr (3:2:1:4).

The acidic strength of catalysts Cu:Zn:Cr:Zr (3:2:1:x) where x=1, 2, 3, 4 was studied by $NH_3$-TPD. Catalysts Cu:Zn:Cr:Zr (3:2:1:3) and Cu:Zn:Cr:Zr (3:2:1:4) show high ammonia desorption in the range of 150-420° C. as compared to Cu:Zn:Cr:Zr (3:2:1:1) and Cu:Zn:Cr:Zr (3:2:1:2). This indicates that Cu:Zn:Cr:Zr (3:2:1:3) and Cu:Zn:Cr:Zr (3:2:1:4) possess higher acidity than Cu:Zn:Cr:Zr (3:2:1:1) and Cu:Zn:Cr:Zr (3:2:1:2). The $NH_3$-TPD profile also shows that with an increase in the zirconia content the acidity of the catalyst is increased (FIG. 13).

Figure 14:
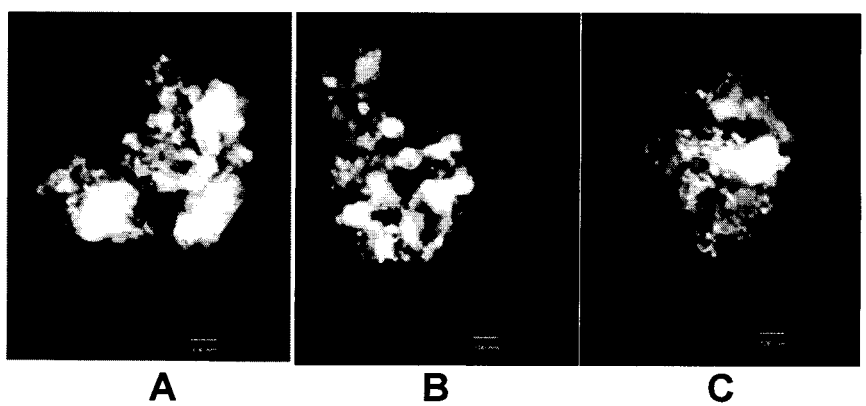
FIG. 14 shows exemplary Transmission Electron Microscopy (TEM) images of fresh catalyst (A), used catalyst (B) and freshly reduced catalyst (C). The scale bar in each of the images has a length of 100 nm.

Transmission Electron Microscopy (TEM) images of fresh, used and freshly reduced Cu:Zn:Cr:Zr (3:2:1:3) are shown in FIG. 14. The fresh catalyst has CuO clusters, while the freshly reduced catalyst has well-dispersed metallic Cu.

The average particle size for metallic Cu was calculated to be 19 nm. The CO-chemisorption results for the Cu metal dispersion, Cu crystalline size and CO adsorbed for the catalysts Cu:Zn:Cr:Zr (3:2:1:x) where x=1, 2, 3, 4 are shown in Table 4. It was observed that with the increase in Zr loading in the catalyst the dispersion of Cu increased, Cu crystalline size decreased and CO intake increased. Therefore, while not wishing to be limited by theory, it can be concluded that zirconium helps in Cu dispersion which might be the reason for the increase in selectivity for 1,2-propandiol. Cu crystalline size measured by CO-chemisorption for Cu:Zn:Cr:Zr (3:2:1:3) was found to be 17 nm which was in accordance with the value obtained from XRD and TEM.

Figure 15:
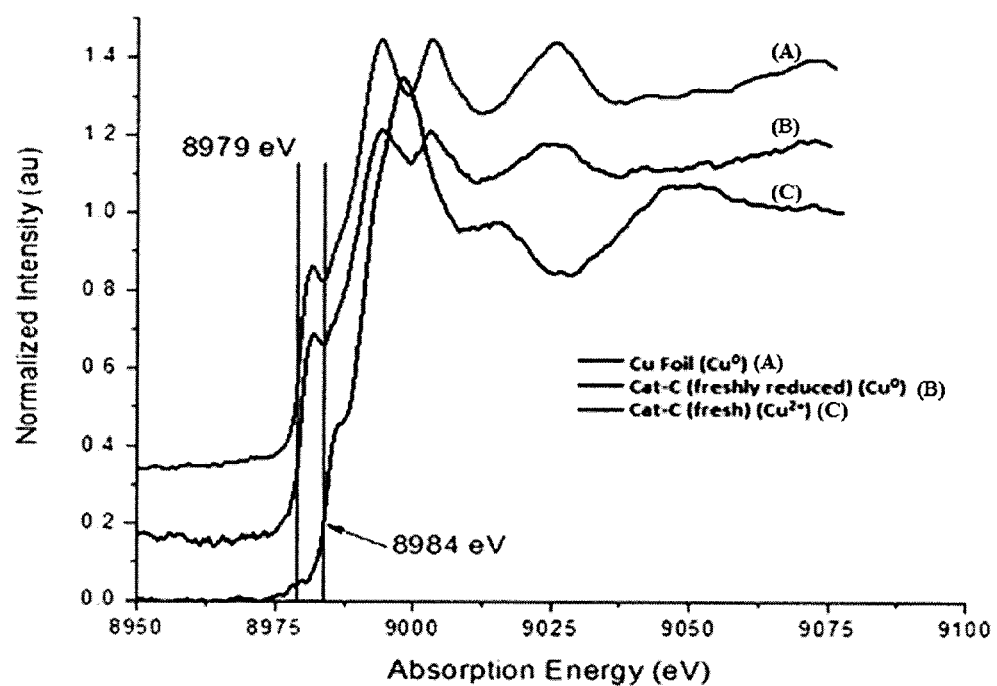
FIG. 15 shows exemplary X-ray Absorption Near Edge Spectroscopy (XANES) spectra: (A) Cu foil, (B) freshly reduced catalyst and (C) fresh catalyst.

X-ray Absorption Near Edge Spectroscopy (XANES) of fresh and freshly reduced Cu:Zn:Cr:Zr (3:2:1:3) catalyst was carried out.[41] The absorption energy for fresh, and freshly reduced catalyst were found to be 8984 eV and 8979 eV, indicating the presence of the $Cu^{2+}$ and $Cu^0$ states of copper (FIG. 15). These results are also in accordance with the XRD data which shows the presence of the $Cu^{2+}$ oxidation state of copper in fresh catalyst as indicated by the presence of CuO, and the $Cu^0$ oxidation state in freshly reduced catalyst as confirmed by the presence of metallic copper.

Catalyst Activity Tests

The catalysts with elemental molar ratios such as Cu:Zn:Cr:Zr (3:2:1:3) were prepared and used in hydrogenolysis of glycerol to propylene glycol. The hydrogenolysis of glycerol follows two routes (i) C—C bond breaking and (ii) C—O bond breaking (FIG. 1). The selective hydrogenolysis of glycerol to 1,2-propylene glycol involves the selective cleavage of C—O bond over the C—C bond cleavage of the glycerol molecule by hydrogen.[45] A Cu:Cr catalyst was prepared by increasing the elemental molar ratio of Cu and investigated for selectivity of propylene glycol. In this study, the Cu:Cr (3:1) catalyst gave values of 40% glycerol conversion and 60% propylene glycol selectivity. The present studies also investigated whether Zn and Zr can be incorporated into the catalyst to enhance glycerol conversion.

The acid-catalyzed hydrogenolysis of glycerol proceeds by a C—O bond breaking step that involves dehydration of glycerol to produce acetol, followed by hydrogenation of acetol to produce 1,2-propylene glycol (FIG. 1).

The Cu:Zn:Cr:Zr (3:2:1:3) catalyst showed 99% glycerol conversion and 97% propylene glycol selectivity which, while not wishing to be limited by theory, could be due to a combined effect of the Cu, Zn, Cr and Zr metal, the metallic Cu dispersion, and the acidity of the catalyst.

Figure 16:
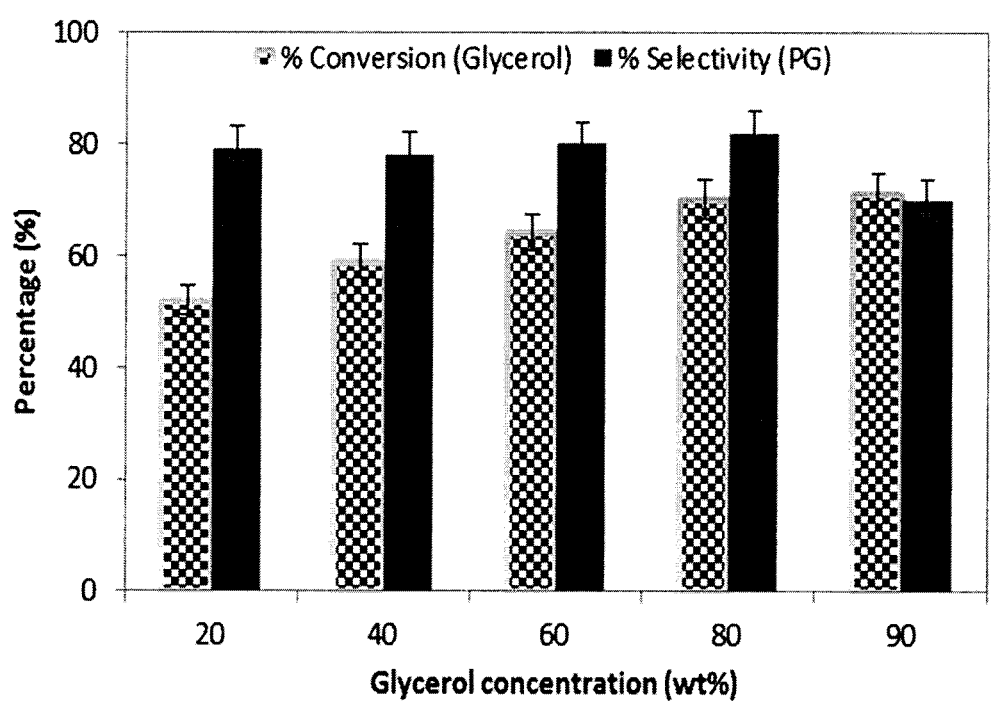
FIG. 16 is a graph showing the effect of glycerol concentration on the % glycerol conversion and % propylene glycol (PG) selectivity: Reaction conditions: glycerol solution: 20-90% w/w, Glycerol flow rate: 10 mL/min, Hydrogen pressure: 800 psi, Hydrogen flow rate: 40 mL/min, Catalyst: 5.0 mL Cu:Zn:Cr:Zr (3:2:1:3), Reaction temperature: 240° C., Time: 24 h, LHSV: 2 h$^{-1}$.

Optimization Study Using Cu:Zn:Cr:Zr (3:2:1:3) Catalyst (a) Effect of Glycerol Concentration Glycerol is a by-product of the biodiesel process and is obtained in different concentrations depending on the isolation procedure used. Hence, different concentrations of glycerol solution such as 20-90 wt % were used to evaluate the activity of the Cu:Zn:Cr:Zr (3:2:1:3) catalyst (FIG. 16).

It was observed that with the increase in glycerol concentration from 20 to 90 wt % the conversion of glycerol is increased, which, while not wishing to be limited by theory, can be due to the presence of more water content at lower glycerol concentration that made Cu:Zn:Cr:Zr (3:2:1:3) catalyst less active. Propylene glycol (PG) selectivity was found to be 96±2% in all cases. Further, experiments were carried out using 80 w/w % of glycerol solution which showed 100% glycerol conversion and 97% propylene glycol selectivity.

(b) Effect of Temperature

Figure 17:
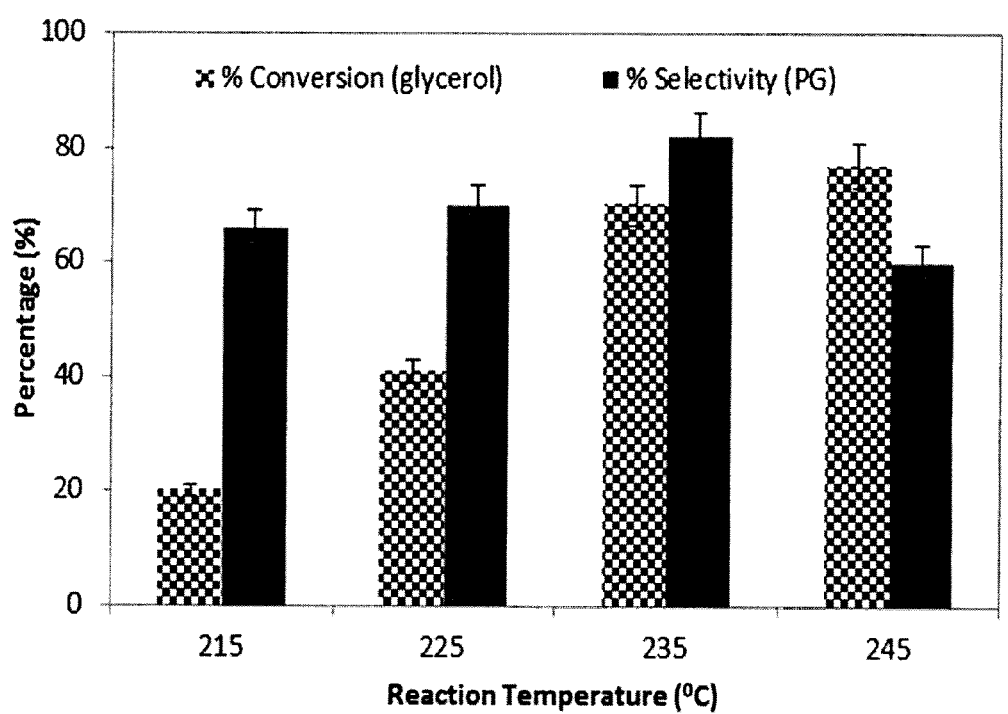
FIG. 17 is a graph showing the effect of temperature on the % glycerol conversion and % propylene glycol (PG) selectivity: Reaction conditions: glycerol solution: 80% w/w, Glycerol flow rate: 10 mL/min, Hydrogen pressure: 800 psi, Hydrogen flow rate: 40 mL/min, Catalyst: 5.0 mL Cu:Zn:Cr:Zr (3:2:1:3), Reaction temperature: 215-245° C., Time: 24 h, LHSV: 2 h$^{-1}$.

The effect of temperature on glycerol conversion and propylene glycol selectivity was studied in the range of 215-245° C. (FIG. 17). It was observed that glycerol conversion increases with an increase in temperature; however, at 245° C. propylene glycol selectivity was found to decrease. Hence, a temperature of 235° C. was selected for further study.

(c) Effect of Glycerol Flow Rate

Figure 18:
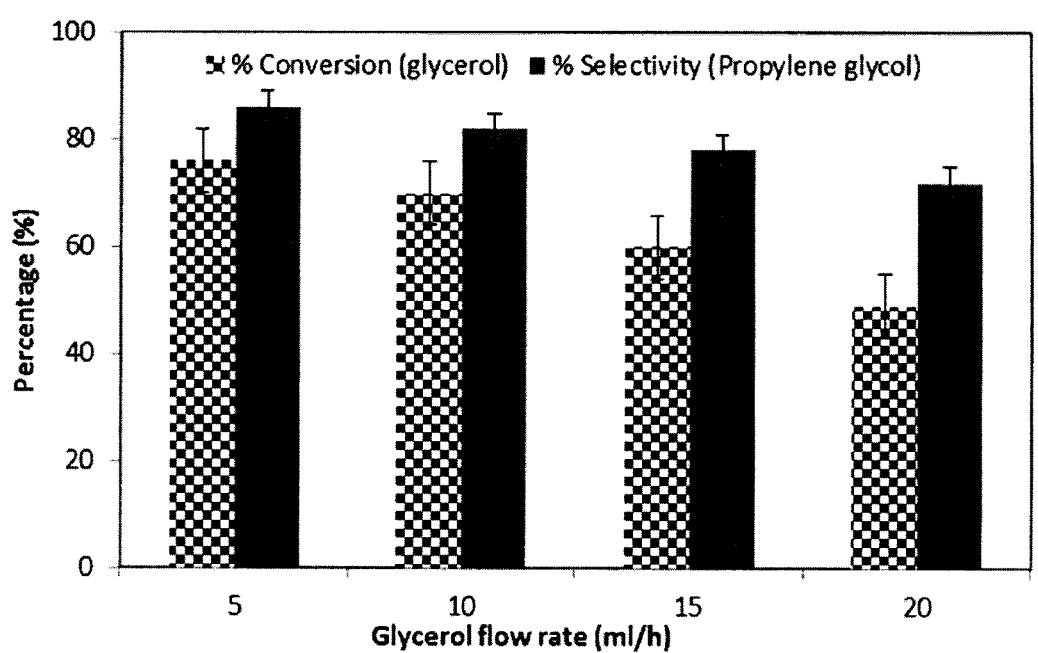
FIG. 18 is a graph showing the effect of glycerol flow rate on the % glycerol conversion and % propylene glycol (PG) selectivity: Reaction conditions: glycerol solution: 80% w/w, Glycerol flow rate: 5-20 mL/h, Hydrogen pressure: 800 psi, Hydrogen flow rate: 40 mL/min, Catalyst: 5.0 mL Cu:Zn:Cr:Zr (3:2:1:3), Reaction temperature: 235° C., Time: 24 h, LHSV: 1-4 h$^{-1}$.

Glycerol flow rate was investigated by conducting the reaction at four different glycerol flow rates of 5, 10, 15 and 20 mL/h with LHSV of 1, 2, 3 and 4 $h^{-1}$ respectively. It was observed that with increasing glycerol flow rate from 15 to 20 mL/h, the conversion and selectivity both decreased (FIG. 18). While not wishing to be limited by theory, the decrease in catalyst activity is due to an increase in LHSV values hence; the residence time of glycerol is decreased. Also, the catalyst to substrate weight ratio is decreased with the increase in feed flow rate so a lower number of catalyst active sites is available to convert glycerol to propylene glycol. Therefore, a 10 mL/h glycerol flow rate was chosen for further reaction parameter investigation.

(d) Effect of Hydrogen Pressure

Figure 19:
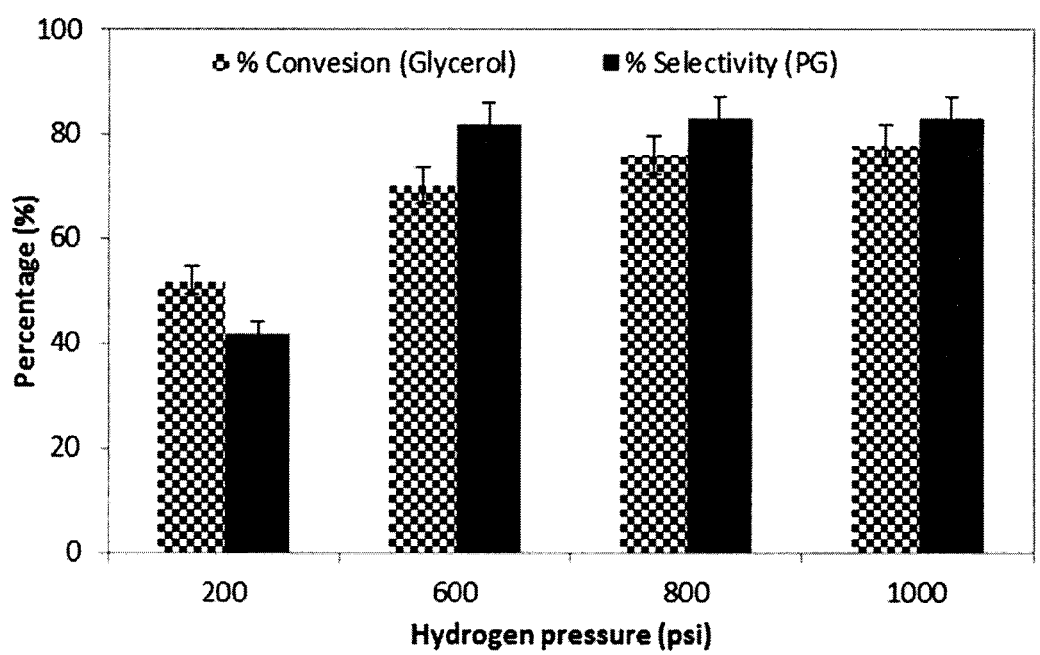
FIG. 19 is a graph showing the effect of hydrogen pressure on the % glycerol conversion and % propylene glycol (PG) selectivity: Reaction conditions: glycerol solution: 80% w/w, Glycerol flow rate: 10 mL/h, Hydrogen pressure: 200-800 psi, Hydrogen flow rate: 40 mL/min, Catalyst: 5.0 mL, Cu:Zn:Cr:Zr (3:2:1:3), Reaction temperature: 235° C., Time: 24 h, LHSV: 2 h$^{-1}$.

The effect of hydrogen pressure on percentage conversion of glycerol and selectivity of propylene glycol were investigated by varying the hydrogen Pressure from 200 to 1000 psi (FIG. 19). It was found that with an increase in the hydrogen pressure, the percentage of glycerol conversion and propylene glycol selectivity increases. As hydrogen solubility in the solution increases with an increase in hydrogen pressure, more hydrogen is available to be adsorbed on catalyst surfaces which can lead to an increase in glycerol conversion. The conversion of glycerol at 800 and 1000 psi was found to be close i.e. 76 and 78, therefore, further reaction studies were carried out at 800 psi of hydrogen pressure.

(e) Effect of Hydrogen Flow Rate

Figure 20:
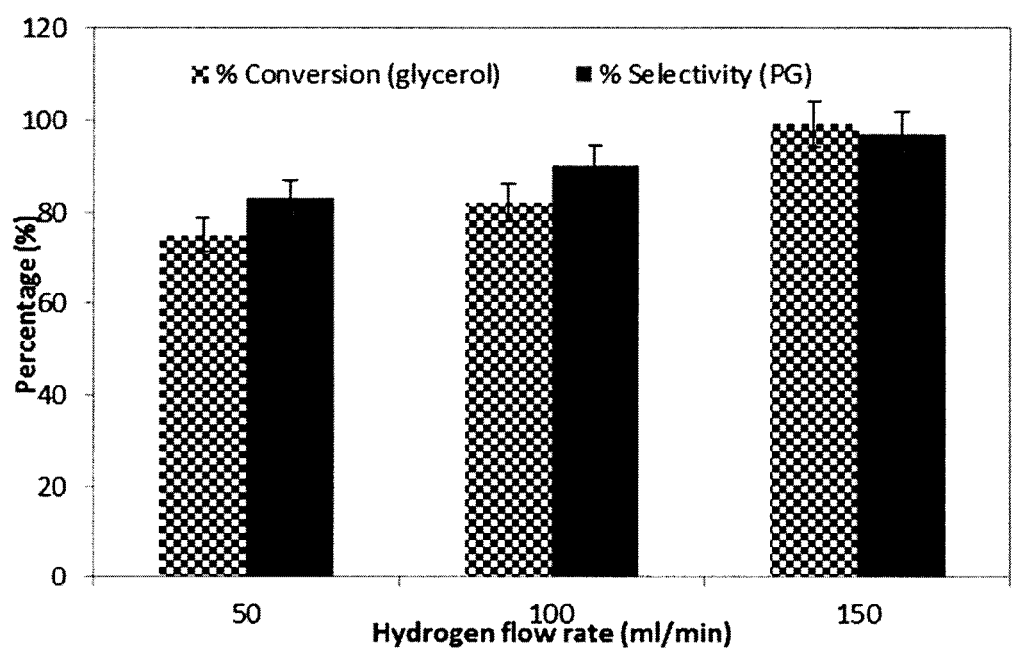
FIG. 20 is a graph showing the effect of hydrogen flow rate on the % glycerol conversion and % propylene glycol (PG) selectivity: Reaction conditions: glycerol solution: 80% w/w, Glycerol flow rate: 10 mL/h, Hydrogen pressure: 800 psi, Hydrogen flow rate: 50-150 mL/min, Catalyst: 5.0 mL Cu:Zn:Cr:Zr (3:2:1:3), Reaction temperature: 235° C., Time: 24 h, LHSV: 2 h$^{-1}$.

Three different $H_2$ flow rates; 50, 100 and 150 mL/h were selected to investigate the effect of the hydrogen flow rate on this reaction. It was observed that with an increase in $H_2$ flow rate from 50 mL/h to 150 mL/h, the glycerol conversion and propylene glycol selectivity increased from 75% to 100%, and 83% to 97%, respectively (FIG. 20). While not wishing to be limited by theory, this increase may be due to the decrease in mass transfer resistance by flushing the excess glycerol from catalyst surface and making the catalyst surface available to hydrogen adsorption. Hence, a 150 mL/min hydrogen flow rate was selected for further study.

(f) the Activity of Pelletized Catalyst Prepared by Using Different Loads

The powdered catalyst was pelletized by applying a load of 2, 4 and 8 tons using a hydraulic pelletizer and the size of pellet was chosen in the range of 1.1 to 1.4 mm. It was observed that catalyst used in pellet form has much lower catalytic activity (75% glycerol conversion) as compared to catalyst used in powdered form (99% glycerol conversion) (Table 5). While not wishing to be limited by theory, this may be due to external mass transfer limitations and channeling effects of the glycerol feed which decreases the glycerol conversion. It was also found that there is not much difference in catalyst activity after applying the different loads to prepare catalyst in pellet form with sizes of 1.14-1.4 mm. Hence; further study was carried out using pelletized catalyst prepared by a 4 ton pressure.

(g) Effect of Catalyst Bed Size (Pelletized Catalyst)

Figure 21:
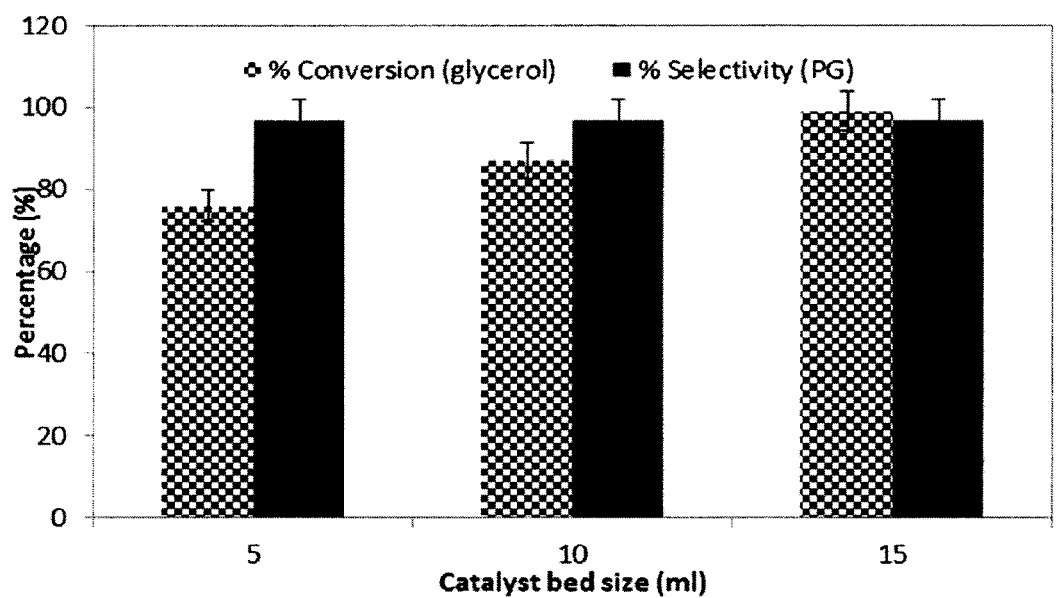
FIG. 21 is a graph showing the effect of catalyst bed size on the % glycerol conversion and % propylene glycol (PG) selectivity: Reaction conditions: glycerol solution: 80% w/w, Glycerol flow rate: 10 mL/h, Hydrogen pressure: 800 psi, Hydrogen flow rate: 150 mL/min, Catalyst: 5.0-15.0 mL pelletized Cu:Zn:Cr:Zr (3:2:1:3), Reaction temperature: 235° C., Time: 24 h, LHSV: 2, 1, 0.67 h$^{-1}$.

The effect of the catalyst bed size on glycerol conversion in a fixed bed reactor was evaluated by using pelletized catalyst bed sizes of 5, 10 and 15 mL with LHSV of 2, 1 and 0.67 $h^{-1}$ (FIG. 21). It was observed that conversion of glycerol increased with an increase in the catalyst bed size from 5 to 15 mL which, while not wishing to be limited by theory, was due to a proportional increase in the number of active sites of the catalyst.

(h) Time on Stream Study with Pelletized Catalyst

Figure 22:
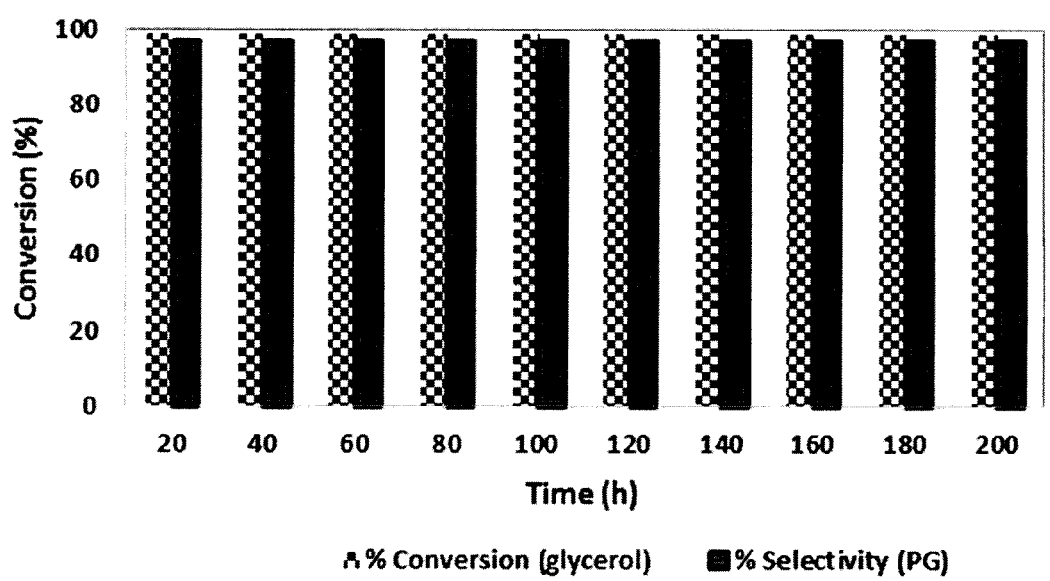
FIG. 22 is a graph showing the results of a time on stream study: Reaction conditions: glycerol solution: 80% w/w, Glycerol flow rate: 10 mL/h, Hydrogen pressure: 800 psi, Hydrogen flow rate: 150 mL/min, Catalyst: 15.0 mL pelletized Cu:Zn:Cr:Zr (3:2:1:3), Reaction temperature: 235° C., Time: 24 h, LHSV: 0.67 h$^{-1}$.

The stability and activity of pelletized Cu:Zn:Cr:Zr (3:2:1:3) catalyst under optimized reaction conditions was evaluated by time on stream (TOS) data up to 200 hours. FIG. 22 shows that the catalyst was stable and active without any loss in glycerol conversion (99%) and propylene selectivity (97%) over this time period.

III. Summary

The Cu:Zn:Cr:Zr (3:2:1:3) catalyst was characterized using XRD, FTIR, $NH_3$-TPD, Py-TPR and CO-chemisorption, TEM, and XANES. A high concentration (80 wt %) of glycerol solution was used to obtain a 99% glycerol conversion and 97% propylene glycol selectivity in a continuous system. The catalytic activity was retained even after 200 hours without affecting the propylene glycol selectivity.

Example 7

Evaluation of Cu:Zn:Cr:Zr (3:2:1:3) Catalyst in Continuous Reactor

I. Summary

The effectiveness of a catalyst to convert glycerol to glycol was evaluated. Operating conditions were varied during the experiment for to study glycerol conversion and glycol yield based on product analysis via HPLC. Suitable reactor conditions determined during the analysis were a hydrogen flow rate of 1.50 L/min, a liquid glycerol solution feed flow rate of 0.40 mL/min, and an average reactor temperature of 233° C.±2° C. on a 120 mL catalyst reactor bed volume. Operating the lab reactor at these conditions produced a glycerol conversion of 99% and a propylene glycol (PG) yield of 64%. These results indicate that the catalyst is a useful catalyst to convert glycerol to glycol.

II. Results and Discussion

Tables 6 and 7 summarize the 21 different operating conditions run on glycerol in the Lab Reactor, and the corresponding product sample numbers.

Conditions 1-19 (Table 6) correspond to the 132 hours for study of the three (3) variables of hydrogen inlet flow rate, operating temperature, and feed flow rate. Conditions C1 and C2 (Table 7) correspond to an additional 11 hours of runtime, in which the glycerol feed concentration was decreased from 80 wt. % to 70 wt. %. The average steady-state glycerol conversions and PG yields are also shown. The average reactor temperatures were calculated from the temperature readings of three thermocouples. This provides a useful representation of operating temperature, since these thermocouples are fully submerged in the catalyst packing segment of the column.

Figure 23:
FIG. 23 is an exemplary photograph of samples obtained from a process according to an embodiment of the present disclosure. These samples were rated to have an average colour of 1 on a colour-coding system wherein on a scale of 1-5, 1 corresponds to a transparent sample with a faint yellow colour and 5 corresponds to a dark orange sample with oily suspended solids.

The colour-coding system applied to the samples is on a scale of 1-5, where 1 corresponds to a desirable transparent sample with a faint yellow colour and 5 corresponds to an undesirable dark orange sample with oily suspended solids. FIG. 23 is an exemplary photograph of samples 139-143. As can be seen in Table 7, these samples were rated to have an average colour of 1 using this colour-coding system.

At conditions that resulted in lower PG yields, a brown coloured by-product is observed and the overall sample colour is also a darker orange colour. Product colour is a useful indicator of product quality because a higher glycerol conversion does not always correspond to a higher quality product, since the glycerol may be partially converting to by-products. Therefore, a suitable operating condition is found through the product with a useful combination of glycerol conversion, PG yield and sample colour rating.

III. Conclusions

Useful operating conditions for the catalyst based on product analysis were determined to be a hydrogen flow rate of 1.5 L/minute, a glycerol solution flow rate of 0.4 mL/min, an average temperature of 233±2° C. and a reactor pressure of 800 psig (5.515 kPa). These conditions produced a glycerol conversion of 99% and a PG yield of 64%. Product quality was determined by a combination of three (3) factors: glycerol conversion, PG yield, and sample colour rating. It was observed that glycerol solution flow rates and hydrogen flow rates have an effect on conversion and yield. At operating temperatures of 233±2° C., the conversion and yield were found to be independent of the temperature. While not wishing to be limited by theory, low hydrogen flow rates were determined to be the cause of low product quality during the first 70 hours of the experiment. At a hydrogen flow rate of 1.5 L/minute, it was determined that product yield increased and that the product samples' colour decreased on the colour coding scale used. It was also found that a 70 wt. % glycerol feedstock resulted in a 15-20% increase in PG yield and a similar glycerol conversion at comparable operating conditions.

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

TABLE 1

Catalyst screening and selection: 100 g of glycerol solution (80%), catalyst of 3% w/w, $H_2$ pressure of 4 MPa, agitation speed of 1000 rpm, temperature of 240° C., 10 h.

| Sr. No. | Catalysts | Elemental molar ratio | % Conv. Glycerol | % Selectivity Propylene glycol | Acetol | Ethylene glycol | Others |
|---|---|---|---|---|---|---|---|
| 1 | Cu:Zn:Ni | 3:2:2 | 42 | 63 | 19 | 9 | 9 |
| 2 | Cu:Cr:Ni | 3:1:2 | 36 | 62 | 10 | 10 | 18 |
| 3 | Cu:Zn:Cr | 3:2:1 | 60 | 80 | 11 | 5 | 4 |
| 4 | Cu:Zn:Cr:Ni | 3:2:1:2 | 38 | 75 | 15 | 5 | 5 |
| 5 | Cu:Zn:Cr:Zr | 3:4:1:3 | 90 | 60 | 5 | 14 | 21 |
| 6 | Cu:Zn:Cr:Zr | 3:2:1:3 | 100 | 97 | 0 | 3 | — |

TABLE 2

Effect of zirconium loading: 100 g of glycerol solution (80%), catalyst of 3% w/w, $H_2$ pressure of 4 MPa, agitation speed of 1000 rpm, temperature of 240° C., 10 h.

| Sr. No. | Catalysts | Elemental molar ratio | % Conversion Glycerol | % Selectivity Propylene glycol | Ethylene glycol | Others |
|---|---|---|---|---|---|---|
| 1 | Cu:Zn:Cr:Zr | 3:2:1:1 | 70 | 97 | 3 | — |
| 2 | Cu:Zn:Cr:Zr | 3:2:1:2 | 81 | 96 | 4 | — |
| 3 | Cu:Zn:Cr:Zr | 3:2:1:3 | 100 | 97 | 3 | — |
| 4 | Cu:Zn:Cr:Zr | 3:2:1:4 | 100 | 83 | 9 | 8 |

TABLE 3

Catalyst reusability: 100 g of glycerol solution (80%), catalyst of 3% w/w, $H_2$ pressure of 4 MPa, agitation speed of 1000 rpm, temperature of 240° C., 10 h.

| Sr. No. | Catalyst | % Conversion Glycerol | % Selectivity Propylene glycol | Ethylene glycol |
|---|---|---|---|---|
| 1 | Fresh | 100 | 97 | 3 |
| 2 | 1st run | 95 | 96 | 4 |
| 3 | 2nd run | 92 | 97 | 3 |
| 4 | 3rd run | 89 | 97 | 3 |
| 5 | 4th run | 86 | 95 | 5 |

TABLE 4

CO-chemisorption study of catalysts Cu:Zn:Cr:Zr (3:2:1:1), Cu:Zn:Cr:Zr (3:2:1:2), Cu:Zn:Cr:Zr (3:2:1:3), and Cu:Zn:Cr:Zr (3:2:1:4).

| Catalyst | Cu metal dispersion (%) | Cu crystalline size (nm) | CO adsorbed (µmole/g) |
|---|---|---|---|
| Cu:Zn:Cr:Zr (3:2:1:1) | 3.2 | 32.6 | 15.1 |
| Cu:Zn:Cr:Zr (3:2:1:2) | 4.2 | 24.5 | 19.9 |
| Cu:Zn:Cr:Zr (3:2:1:3) | 5.8 | 17.0 | 27.8 |
| Cu:Zn:Cr:Zr (3:2:1:4) | 6.1 | 16.6 | 28.4 |

TABLE 5

Activity of catalyst prepared by using different loads: Reaction conditions: glycerol solution: 80% w/w, Glycerol flow rate: 10 mL/h, Hydrogen pressure: 800 psi, Hydrogen flow rate: 150 mL/min, Catalyst: 5.0 mL, Reaction temperature: 235° C., Time: 24 h, LHSV: 2 h$^{-1}$.

| Sr. No. | Load applied to make pellets (Ton) | % Conversion (glycerol) | % Selectivity (propylene glycol) | BET surface area (m²/g) | BJH pore volume (cm³/g) | BJH average pore size (Å) |
|---|---|---|---|---|---|---|
| 1 | 0 (Powder form) | 99 | 97 | 12.64 | 0.20 | 343.9 |
| 2 | 2 | 78 | 97 | 17.63 | 0.16 | 249.2 |
| 3 | 4 | 76 | 97 | 18.75 | 0.13 | 251.8 |
| 4 | 8 | 75 | 97 | 16.82 | 0.15 | 264.4 |

TABLE 6

Summary of Reactor Operating Conditions and Product Results

| No. | Start Time | End Time | Samples | $H_2$ Flow (L/min) | Glycerol Feed Flow Rate (mL/min) |
|---|---|---|---|---|---|
| 1 | 2013-12-16 17:00 | 2013-12-16 19:00 | 2-4 | 0.40 | 1.12 |
| 2 | 2013-12-16 20:00 | 2013-12-17 0:00 | 5-9 | 0.35 | 1.12 |
| 3 | 2013-12-17 1:00 | 2013-12-17 11:00 | 10-19 | 0.22 | 1.12 |
| 4 | 2013-12-17 11:00 | 2013-12-18 9:00 | 20-48 | 0.22 | 1.12 |
| 5 | 2013-12-18 10:00 | 2013-12-18 20:00 | 49-52 | 0.28 | 0.52 |
| 6 | 2013-12-18 22:00 | 2013-12-19 1:00 | 53-56 | 0.28 | 0.28 |
| 7 | 2013-12-19 2:00 | 2013-12-19 4:00 | 57-59 | 0.28 | 0.28 |

TABLE 6-continued

Summary of Reactor Operating Conditions and Product Results

| | | | | | |
|---|---|---|---|---|---|
| 8 | 2013-12-19 5:00 | 2013-12-19 8:00 | 60-63 | 0.28 | 0.28 |
| 9 | 2013-12-19 9:00 | 2013-12-19 15:00 | 64-70 | 0.28 | 0.28 |
| 10 | 2013-12-19 16:00 | 2013-12-19 20:00 | 71-74 | 1.00 | 0.28 |
| 11 | 2013-12-19 21:00 | 2013-12-20 4:00 | 75-82 | 1.00 | 0.21 |
| 12 | 2013-12-19 22:00 | 2013-12-20 18:00 | 82-88 | 1.00 | 0.52 |
| 13 | 2013-12-20 21:00 | 2013-12-22 8:00 | 89-100 | 1.00 | 0.21 |
| 14 | 2013-12-22 9:00 | 2013-12-22 13:00 | 101-105 | 1.00 | 0.29 |
| 15 | 2013-12-22 14:00 | 2013-12-22 17:00 | 106-108 | 1.50 | 0.29 |
| 16 | 2013-12-22 18:00 | 2013-12-22 23:00 | 109-113 | 1.50 | 0.40 |
| 17 | 2013-12-23 0:00 | 2013-12-23 5:00 | 114-119 | 1.80 | 0.55 |
| 18 | 2013-12-23 6:00 | 2013-12-23 11:30 | 120-125 | 2.00 | 0.78 |
| 19 | 2013-12-23 12:30 | 2013-12-24 2:00 | 126-132 | 1.50 | 0.40 |

| Average Reactor Temperature (° C.) | Standard Deviation of Temperature Across the Reactor (±° C.) | Main Variable(s) Changed | Average Color | Average Steady State Glycerol Conversion (%) | Average Steady State PG Yield (%) |
|---|---|---|---|---|---|
| 216 | 8 | — | 5 | 59 | 9 |
| 223 | 14 | H$_2$ flow | 5 | 55 | 22 |
| 226 | 11 | H$_2$ flow, temperature | 4 | 60 | 21 |
| 213 | 13 | temperature | 3 | 45 | 25 |
| 213 | 7 | feed flow | 3 | 46 | 30 |
| 218 | 9 | feed flow | 3 | 47 | 32 |
| 225 | 11 | temperature | 4 | 78 | 31 |
| 230 | 12 | temperature | 5 | 87 | 27 |
| 236 | 8 | temperature | 5 | 96 | 21 |
| 233 | 5 | H$_2$ flow, temperature | 3 | 99 | 44 |
| 232 | 5 | feed flow | 1 | 100 | 59 |
| 233 | 4 | feed flow | 2 | 78 | 34 |
| 232 | 4 | feed flow | 2 | 99 | 47 |
| 232 | 5 | feed flow | 1 | 100 | 61 |
| 233 | 4 | H$_2$ flow | 1 | 100 | 59 |
| 233 | 8 | feed flow, temperature | 1 | 99 | 64 |
| 235 | 9 | feed flow, temperature | 1 | 90 | 51 |
| 235 | 14 | feed flow, temperature | 2 | 85 | 45 |
| 233 | 10 | feed flow, temperature | 1 | 94 | 52 |

TABLE 7[1]

| | No. | |
|---|---|---|
| | C1 | C2 |
| Start Time | 2013-12-23 22:00 | 2013-12-24 4:00 |
| End Time | 2013-12-24 3:00 | 2013-12-24 8:00 |
| Samples (Inclusive) | 133-138 | 139-143 |
| H$_2$ Flow (L/min) | 1.51 | 1.51 |
| Feed Flow Rate (mL/min) | 0.40 | 0.51 |
| Temperature Set Point (° C.) | 232 | 233 |
| Standard Deviation of Reactor Temperature (±° C.) | 11 | 11 |
| Main Variable(s) Changed | Feed | feed flow, temperature |
| Average Color | 1 | 1 |
| Average Steady State Glycerol Conversion (%) | 95 | 92 |
| Average Steady State PG Yield (%) | 79 | 75 |

[1]Glycerol feed concentration changed to 70 wt %.

FULL CITATIONS FOR DOCUMENTS REFERRED TO IN THE APPLICATION

1 Roy, D.; Subramaniam, B.; Chaudhari, R. V. *Catalysis Today* 2010, 156, 31.
2 Yuan, Z.; Wang, J.; Wang, L.; Xie, W.; Chen, P.; Hou, Z.; Zheng, X. *Bioresource Technology* 2010, 101, 7088.
3 Balaraju, M.; Rekha, V.; Prabhavathi Devi, B. L. A.; Prasad, R. B. N.; Sai Prasad, P. S.; Lingaiah, N. *Applied Catalysis A: General* 2010, 384, 107.
4 Vasiliadou, E.; Lemonidou, A. *Org. Process Res. Dev.* 2011, 15, 925.
5 Meher, L. C.; Gopinath, R.; Naik, S. N.; Dalai, A. K. *Ind, Eng. Chem. Res.* 2009, 48, 1840.
6 Ma, F.; Hanna, M. A. *Biores. Technol.* 1999, 70, 1.
7 Werpy, G. P. Results of Screening for Potential Candidates from Sugars and Synthesis Gas. *US DOE Report* 2004, Vol. 1.
8 Zhou, C. H.; Beltramini, J. N.; Fana, Y. X.; Lu, G. Q. *J. Chem. Soc. Rev,* 2008, 37, 527.
9 Wang, Z. J.; Zhuge, J.; Fang, H.; Prior, B. A. *Biotechnol. Adv.* 2001, 19, 201.
10 Akiyama, M.; Sato, S; Takahashi, R.; Inui, K.; Yokota, M. *Appl. Catal. A: Gen.* 2009, 371, 60.
11 Cortright, R. D.; Sanchez-Castillo, M.; Dumesic, J. A. *Appl. Catal. B* 2002, 39, 353.
12 Perrin, R.; Scharff, J. P. *Chimie industrielle,* 1993, Masson Ed.
13 Hao, S.; Peng, W.; Zhao, N.; Xiao, F.; Wei, W.; Suna, Y.; *J Chem. Technol. Biotechnol.* 2010, 85, 1499.
14 Che, T. M. Celanese Corp. Production of propanediols. U.S. Pat. No. 4,642,394, 1987.
15 Drent, E.; Jager, W. W.; Shell Oil Co. Hydrogenolysis of glycerol. U.S. Pat. No. 6,080,898, 2000.
16 Schlaf, M.; Ghosh, P.; Fagan, P. J.; Hauptman, E.; Bullock, R. M.; *Angew. Chem. Int. Ed.* 2001, 40(20), 3887.
17 Dasari, M. A.; Kiatsimkul, P. P.; Sutterlin, W. R.; Suppes, G. J. *Appl. Catal. A: Gen.* 2005, 281(1-2), 225.
18 Harrison, R. Nuffield Advanced Science Book of Data; Longman: London, 1972.
19 Mane, R. B.; Hengne, A. M.; Ghalwadkar, A. A.; Vijayanand, S.; Mohite, P. H.; Potdar, H. S.; Rode, C. V. *Catal. Lett.* 2010, 135, 141.

20. Montassier, C.; Menezo, J. C.; Moukolo, J.; Naja, J.; Hoang, L. C.; Barbier, J. *J. Mol. Catal.* 1991, 70(1), 99.
21. Montassier, C.; Dumas, J. M.; Granger, P.; Barbier, J. *J. Appl. Catal. A* 1995, 121(2), 231.
22. Schmidt, S. R.; Tanielyan, S. K.; Marin. N.; Alvez, G.; Augustine, R. L. *Top. Catal.* 2010, 53, 1214.
23. Werpy, T.; Frye, J.; Zacher, A.; Miller, D. Hydrogenolysis of 6-carbon sugars and other organic compounds. Int. Patent WO03035582 B1, 2003.
24. Maris, E. P.; Ketchic, W. C.; Murayama, M.; Davis, R. J. *J. Catal.* 2007, 251(2), 281.
25. Gandarias, I.; Arias, P. L.; Requies, J.; Guemez, M. B.; Fierro, J. L. G.; *Applied Catalysis B: Environmental* 2010, 97, 248.
26. Chaminand, J.; Djakovitch, L.; Gallezot, P.; Marion, P.; Pinel, C.; Rosier, C. *Green Chem.* 2004, 6, 359.
27. Maris, E. P.; Davis, R. J. *J. Catal.* 2007, 249, 328.
28. Moulton, K.; Beal, R. Nickel/copper chromite catalysts for hydrogenating edible oils. U.S. Pat. No. 3,856,710, 1974.
29. Suppes, G.; Sutterlin, W.; Dasari, M. Methods of producing lower alcohols from glycerol. US Patent Application 2005/0244312, 2005.
30. T. Miyazawa, Y. Kusunoki, K. Kunimori, K. Tomishige, J. Catal. 240 (2006) 213-221.
31. T. Miyazawa, S. Koso, K. Kunimori, K, Tomishige, Appl Catal. A: Gen. 318 (2007) 244.
32. R. Burch, S. E. Golunski, M. S. Spencer, J. Chem. Soc., Faraday Trans. 86 (1990) 2683-2691.
33. U. Pillai, S. Deevi, Appl Catal. B: Environ. 65 (2006) 110-117.
34. Raju, G.; Reddy, P. S.; Reddy, B. M. *Catalysis Journal* 2011, 4, 83.
35. G. Raju, P. S. Reddy, B. M. Reddy, The open Catal. J. 4 (2011) 83-87.
36. C. Zhang, T. Liu, H. Wang, F. Wang, X. Pan, Chem. Eng. J. 174 (2011) 236-241.
37. X. Shi, Y. Wu, P. Li, H. Yi, M. Yang, G. Wang, Carbohydr. Res. 346 (2011) 480-487.
38. E. Liu, A. J. Locke, R. L. Frost, W. N. Martens, J. Mol. Catal. A Chem. 353 (2012) 95-105.
39. B. Azambrea, L. Zenbourya, P. Da Costab, S. Capelac, S. Carpentierc, A. Westermanna, Catal. Today 176 (2011) 242-249.
40. Lahr, D. G.; Shanks, B. H. *J. Catal.* 2005, 232, 386.
41. R. V. Sharma, U. Das, R. Sammynaiken, A. K. Dalai, Appl Catal. A: Gen. 454 (2013) 127-136.
42. C. M. Phillippi, K. S. Mazdiyasni, J. Am. Ceram. Soc. 54 (1971) 254-258.
43. G. D. Yadav, A. D. Murkute, J. Catal. 224 (2004) 218-223.
44. L. Shi, K. Tao, R. Yang, F. Meng, C. Xing, N. Tsubaki, Appl Catal. A: Gen. 401 (2011) 46-55.
45. D. G. Lahr, B. H. Shanks, Ind. Eng. Chem. Res. 42 (2003) 5467-5472.

We claim:

1. A process for the hydrogenolysis of glycerol to produce propylene glycol comprising:
   (a) contacting the glycerol with hydrogen in the presence of a heterogeneous catalyst under conditions for the formation of propylene glycol; and
   (b) optionally isolating the propylene glycol, wherein the heterogeneous catalyst comprises Cu, Cr, Zn and Zr.

2. The process of claim 1, wherein the propylene glycol is formed as the major product in the process.
3. The process of claim 2, wherein the propylene glycol is formed with a selectivity of greater than 90%.
4. The process of claim 1, wherein the catalyst is prepared using a co-precipitation method.
5. The process of claim 1 to wherein the heterogeneous catalyst comprises Cu, Zn, Cr and Zr in an elemental molar ratio (Cu:Zn:Cr:Zr) of 3:2:1:1, 3:2:1:2, 3:2:1:3 or 3:2:1:4.
6. The process of claim 1, wherein the glycerol is a solution comprising at least about 50% (w/w) glycerol.
7. The process of claim 6, wherein the glycerol is an aqueous solution comprising about 60% (w/w) to about 90% (w/w) glycerol.
8. The process of claim 1, wherein the glycerol is crude glycerol obtained as a byproduct from the production of biodiesel.
9. The process of claim 1, wherein the conditions for the formation of propylene glycol comprise use of a catalyst loading of about 1% (w/w) to about 5% (w/w).
10. The process of claim 1, wherein the conditions for the formation of propylene glycol comprise use of an $H_2$ pressure of about 1 MPa to about 10 MPa.
11. The process of claim 1, wherein the conditions for the formation of propylene glycol comprise use of a temperature of about 150° C. to about 300° C.
12. The process of claim 1, wherein the conditions for the formation of propylene glycol comprise use of an agitation speed of about 500 rpm to about 1500 rpm.
13. A process for producing propylene glycol comprising:
    (a) contacting glycerol with hydrogen in the presence of a heterogeneous catalyst under conditions for the formation of propylene glycol; and
    (b) optionally isolating the propylene glycol,
    wherein the heterogeneous catalyst comprises Cu, Zn, Cr and Zr.
14. The process of claim 1, wherein the process is performed in a continuous format.
15. The process of claim 1, wherein the heterogeneous catalyst is reused at least 1 time.
16. The process of claim 1, wherein the heterogeneous catalyst is reduced prior to the contacting with glycerol in the presence of hydrogen.
17. A composition comprising a heterogeneous catalyst, glycerol, water and hydrogen gas, wherein the heterogeneous catalyst comprises Cu, Zn, Cr and Zr.
18. The composition of claim 17, wherein the heterogeneous catalyst comprises Cu, Zn, Cr and Zr in an elemental molar ratio (Cu:Zn:Cr:Zr) of 3:2:1:1, 3:2:1:2, 3:2:1:3 or 3:2:1:4.
19. The composition of claim 18, wherein the heterogeneous catalyst comprises Cu, Zn, Cr and Zr in an elemental molar ratio (Cu:Zn:Cr:Zr) of 3:2:1:3 or 3:2:1:4.
20. The composition of claim 19, wherein the heterogeneous catalyst comprises Cu, Zn, Cr and Zr in an elemental molar ratio (Cu:Zn:Cr:Zr) of 3:2:1:3.
21. The process of claim 1, wherein the heterogeneous catalysts consists essentially of Cu, Cr, Zn and Zr.
22. The process of claim 13, wherein the heterogeneous catalysts consists essentially of Cu, Cr, Zn and Zr.
23. The composition of claim 17, wherein the heterogeneous catalysts consists essentially of Cu, Cr, Zn and Zr.

* * * * *

UNITED STATES PATENT AND TRADEMARK OFFICE
CERTIFICATE OF CORRECTION

PATENT NO. : 9,464,015 B2
APPLICATION NO. : 14/769112
DATED : October 11, 2016
INVENTOR(S) : Dalai et al.

It is certified that error appears in the above-identified patent and that said Letters Patent is hereby corrected as shown below:

In the Specification

"C. 2°" Column 7, Line 6, should read --"C $\pm$ 2°"--.

"Cu:Zn:Car" Column 7, Line 7, should read --"Cu:Zn:Cr:Zr"--.

"detector (FED)" Column 10, Line 54, should read --"detector (FID)"--.

"time of 5 min, 1 ml" Column 10, Line 62, should read --"time of 5 min, 1 µL"--.

"copper (H)" Column 13, Line 38, should read --"copper (II)"--.

In the Claims

"The process of claim 1 to wherein" Column 26, Line 7, Claim 5, should read --"The process of claim 1, wherein"--.

Signed and Sealed this
Third Day of January, 2017

Michelle K. Lee
*Director of the United States Patent and Trademark Office*